United States Patent
Hansen et al.

(10) Patent No.: US 12,075,981 B2
(45) Date of Patent: *Sep. 3, 2024

(54) SET COMPRISING A SURGICAL INSTRUMENT

(71) Applicant: Cilag GMBH International, Zug (CH)

(72) Inventors: Steen Møller Hansen, Los Gatos, CA (US); Henriette Schultz Kirkegaard, Copenhagen (DK)

(73) Assignee: Cilag GmbH International, Zug (CH)

( * ) Notice: Subject to any disclaimer, the term of this patent is extended or adjusted under 35 U.S.C. 154(b) by 603 days.

This patent is subject to a terminal disclaimer.

(21) Appl. No.: 17/330,642

(22) Filed: May 26, 2021

(65) Prior Publication Data

US 2021/0345871 A1    Nov. 11, 2021

Related U.S. Application Data

(63) Continuation of application No. 15/120,256, filed as application No. PCT/DK2015/050035 on Feb. 20, 2015, now Pat. No. 11,033,182.

(30) Foreign Application Priority Data

Feb. 21, 2014  (EP) .................................. 14156155
Nov. 20, 2014  (DK) .......................... PA 2014 70716

(51) Int. Cl.
*A61B 1/06*     (2006.01)
*A61B 1/018*    (2006.01)
(Continued)

(52) U.S. Cl.
CPC ............ *A61B 1/0605* (2022.02); *A61B 1/018* (2013.01); *A61B 1/0625* (2022.02);
(Continued)

(58) Field of Classification Search
CPC ................ A61B 1/0605; A61B 1/0625; A61B 17/062; A61B 17/29; A61B 90/30; A61B 2090/309; A61B 2090/366
(Continued)

(56) References Cited

U.S. PATENT DOCUMENTS 3,919,541 A    11/1975  Chao
4,694,434 A     9/1987  Von et al.
(Continued)

FOREIGN PATENT DOCUMENTS

CA    2603353 A1    9/2007
CN    2533818 Y     2/2003
(Continued)

OTHER PUBLICATIONS

U.S. Appl. No. 15/717,088, filed Sep. 27, 2017, Minimally Invasive Surgery System.
(Continued)

*Primary Examiner* — Joseph M Dietrich
*Assistant Examiner* — Michael T. Holtzclaw
(74) *Attorney, Agent, or Firm* — Mintz Levin Cohn Ferris Glovsky and Popeo, P.C.

(57) ABSTRACT

The invention relates to a correlated set for minimal invasive surgery comprising a surgical instrument and a pattern generating member, a surgical system, a training kit, a method of training and a method of performing a minimal invasive surgery. The surgical instrument comprises a handle portion, a surgical tool and a body portion connecting the handle portion to the surgical tool. The pattern generating member comprises a pattern light source and a projector for projecting a light pattern. The projector is adapted for being at least temporarily fixed to the body portion of the surgical instrument such that a movement of said surgical tool results in a correlated movement of said projector.

13 Claims, 11 Drawing Sheets

(51) Int. Cl.
  *A61B 1/313* (2006.01)
  *A61B 17/062* (2006.01)
  *A61B 17/28* (2006.01)
  *A61B 17/29* (2006.01)
  *A61B 90/30* (2016.01)
  *A61B 17/00* (2006.01)
  *A61B 90/00* (2016.01)
  *G09B 9/00* (2006.01)

(52) U.S. Cl.
  CPC ............ *A61B 1/0655* (2022.02); *A61B 1/313* (2013.01); *A61B 1/3132* (2013.01); *A61B 17/062* (2013.01); *A61B 17/28* (2013.01); *A61B 17/29* (2013.01); *A61B 17/2909* (2013.01); *A61B 90/30* (2016.02); *A61B 2017/00734* (2013.01); *A61B 2017/00849* (2013.01); *A61B 2090/309* (2016.02); *A61B 2090/3614* (2016.02); *A61B 2090/366* (2016.02); *G09B 9/00* (2013.01)

(58) Field of Classification Search
  USPC .................................................. 606/1
  See application file for complete search history.

(56) References Cited

U.S. PATENT DOCUMENTS

| | | |
|---|---|---|
| 4,877,016 A | 10/1989 | Kantor et al. |
| 4,887,222 A | 12/1989 | Miyake et al. |
| 5,457,439 A | 10/1995 | Kuhn |
| 5,588,949 A | 12/1996 | Taylor et al. |
| 5,651,783 A | 7/1997 | Reynard |
| 5,710,870 A | 1/1998 | Ohm et al. |
| 5,725,523 A | 3/1998 | Mueller |
| 5,747,953 A | 5/1998 | Philipp |
| 5,754,717 A | 5/1998 | Esch |
| 5,769,791 A | 6/1998 | Benaron et al. |
| 5,836,869 A | 11/1998 | Kudo et al. |
| 5,888,194 A | 3/1999 | Utsumi et al. |
| 5,933,223 A | 8/1999 | Flock et al. |
| 5,951,142 A | 9/1999 | Wang et al. |
| 5,976,077 A | 11/1999 | Wittens et al. |
| 5,989,181 A | 11/1999 | Duetting et al. |
| 6,006,127 A | 12/1999 | Van et al. |
| 6,017,354 A | 1/2000 | Culp et al. |
| 6,036,636 A | 3/2000 | Motoki et al. |
| 6,165,184 A | 12/2000 | Verdura et al. |
| 6,361,530 B1 | 3/2002 | Mersch |
| 6,387,044 B1 | 5/2002 | Tachibana et al. |
| 6,471,638 B1 | 10/2002 | Chang et al. |
| 6,494,827 B1 | 12/2002 | Matsumoto et al. |
| 6,503,195 B1 | 1/2003 | Keller et al. |
| 6,522,806 B1 | 2/2003 | James et al. |
| 6,527,704 B1 | 3/2003 | Chang et al. |
| 6,537,290 B2 | 3/2003 | Adams et al. |
| 6,549,288 B1 | 4/2003 | Migdal et al. |
| 6,631,271 B1 | 10/2003 | Logan |
| 6,659,943 B2 | 12/2003 | Watanabe et al. |
| 6,741,883 B2 | 5/2004 | Gildenberg |
| 6,791,601 B1 | 9/2004 | Chang et al. |
| 6,810,184 B2 | 10/2004 | Skutnik |
| 6,811,546 B1 | 11/2004 | Callas et al. |
| 6,908,428 B2 | 6/2005 | Aizenfeld et al. |
| 6,945,981 B2 | 9/2005 | Donofrio et al. |
| 7,037,314 B2 | 5/2006 | Armstrong |
| 7,049,594 B2 | 5/2006 | Wu et al. |
| 7,063,695 B2 | 6/2006 | Nield et al. |
| 7,113,675 B2 | 9/2006 | Nield et al. |
| 7,211,044 B2 | 5/2007 | Mast et al. |
| 7,422,327 B2 | 9/2008 | Smith |
| 7,464,846 B2 | 12/2008 | Shelton et al. |
| 7,505,808 B2 | 3/2009 | Anderson et al. |
| 7,725,214 B2 | 5/2010 | Diolaiti |
| 7,775,969 B2 | 8/2010 | Teichmann |
| 7,784,947 B2 | 8/2010 | Perez et al. |
| 7,843,558 B2 | 11/2010 | Furman |
| 7,845,537 B2 | 12/2010 | Shelton et al. |
| 7,876,942 B2 | 1/2011 | Gilboa |
| 7,912,532 B2 | 3/2011 | Schmidt et al. |
| 7,927,272 B2 | 4/2011 | Bayer et al. |
| 7,976,459 B2 | 7/2011 | Laser |
| 8,064,819 B2 | 11/2011 | Ingrassia et al. |
| 8,086,008 B2 | 12/2011 | Coste-Maniere et al. |
| 8,162,826 B2 | 4/2012 | Pecherer et al. |
| 8,165,351 B2 | 4/2012 | Bendall |
| 8,182,422 B2 | 5/2012 | Bayer et al. |
| 8,211,044 B2 | 7/2012 | Liebowitz |
| 8,242,390 B2 | 8/2012 | Prest et al. |
| 8,242,398 B2 | 8/2012 | Young et al. |
| 8,340,379 B2 | 12/2012 | Razzaque et al. |
| 8,397,335 B2 | 3/2013 | Gordin et al. |
| 8,403,843 B2 | 3/2013 | Bruto |
| 8,409,076 B2 | 4/2013 | Pang et al. |
| 8,443,007 B1 | 5/2013 | Kindig et al. |
| 8,480,566 B2 | 7/2013 | Farr |
| 8,512,368 B2 | 8/2013 | Sato et al. |
| 8,525,059 B2 | 9/2013 | Berger et al. |
| 8,527,033 B1 | 9/2013 | Williams et al. |
| 8,531,511 B2 | 9/2013 | Katakura |
| 8,554,307 B2 | 10/2013 | Razzaque et al. |
| 8,568,304 B2 | 10/2013 | Vayser et al. |
| 8,632,535 B2 | 1/2014 | Shelton et al. |
| 8,657,809 B2 | 2/2014 | Schoepp |
| 8,670,816 B2 | 3/2014 | Green et al. |
| 8,672,207 B2 | 3/2014 | Shelton et al. |
| 8,708,211 B2 | 4/2014 | Zemlok et al. |
| 8,721,525 B2 | 5/2014 | Heckele et al. |
| 8,750,568 B2 | 6/2014 | Frank et al. |
| 8,780,362 B2 | 7/2014 | Sharonov et al. |
| 8,880,151 B1 | 11/2014 | Stolka et al. |
| 8,892,191 B2 | 11/2014 | Brennan et al. |
| 8,922,781 B2 | 12/2014 | Tearney et al. |
| 8,968,347 B2 | 3/2015 | Mccollam |
| 8,988,505 B2 | 3/2015 | Schaerer et al. |
| 9,008,757 B2 | 4/2015 | Wu |
| 9,179,984 B2 | 11/2015 | Teichman et al. |
| 11,020,144 B2 | 6/2021 | Hansen et al. |
| 11,033,182 B2 | 6/2021 | Hansen et al. |
| 11,039,734 B2 | 6/2021 | Hansen et al. |
| 2001/0025174 A1 | 9/2001 | Daniel et al. |
| 2001/0027272 A1 | 10/2001 | Saito et al. |
| 2001/0040990 A1 | 11/2001 | Dadi |
| 2001/0055462 A1 | 12/2001 | Seibel |
| 2002/0028986 A1 | 3/2002 | Thompson |
| 2002/0049435 A1 | 4/2002 | Mersch |
| 2002/0049464 A1 | 4/2002 | Donofrio et al. |
| 2002/0087179 A1 | 7/2002 | Culp et al. |
| 2002/0123665 A1 | 9/2002 | Miller |
| 2002/0137987 A1 | 9/2002 | Watanabe et al. |
| 2003/0013960 A1 | 1/2003 | Makin et al. |
| 2003/0029464 A1 | 2/2003 | Chen et al. |
| 2003/0095781 A1 | 5/2003 | Williams |
| 2003/0118302 A1 | 6/2003 | James et al. |
| 2004/0022527 A1 | 2/2004 | Carusillo et al. |
| 2004/0064019 A1 | 4/2004 | Chang et al. |
| 2004/0092794 A1 | 5/2004 | Chin et al. |
| 2004/0122292 A1 | 6/2004 | Dey et al. |
| 2004/0145746 A1 | 7/2004 | Kim et al. |
| 2004/0188616 A1 | 9/2004 | Wu et al. |
| 2005/0004592 A1 | 1/2005 | Criscuolo |
| 2005/0005024 A1 | 1/2005 | Samuels et al. |
| 2005/0054894 A1 | 3/2005 | Aizenfeld et al. |
| 2005/0085718 A1 | 4/2005 | Shahidi |
| 2005/0131426 A1 | 6/2005 | Moctezuma et al. |
| 2005/0135749 A1 | 6/2005 | Nield et al. |
| 2006/0004406 A1 | 1/2006 | Wehrstein et al. |
| 2006/0036162 A1 | 2/2006 | Shahidi et al. |
| 2006/0069314 A1 | 3/2006 | Farr |
| 2006/0114473 A1 | 6/2006 | Tearney et al. |
| 2006/0171693 A1 | 8/2006 | Todd et al. |
| 2006/0235270 A1 | 10/2006 | Teichmann |
| 2006/0235279 A1 | 10/2006 | Hawkes et al. |
| 2006/0241347 A1 | 10/2006 | Whitehead |

(56) References Cited

U.S. PATENT DOCUMENTS

| | | |
|---|---|---|
| 2006/0258938 A1 | 11/2006 | Hoffman et al. |
| 2007/0060098 A1 | 3/2007 | Mccoy |
| 2007/0112336 A1 | 5/2007 | Aizenfeld et al. |
| 2007/0112337 A1 | 5/2007 | Salman et al. |
| 2007/0147707 A1 | 6/2007 | Coste-maniere et al. |
| 2007/0151390 A1 | 7/2007 | Blumenkranz et al. |
| 2007/0167679 A1 | 7/2007 | Miyamoto et al. |
| 2007/0175964 A1 | 8/2007 | Shelton et al. |
| 2007/0179488 A1 | 8/2007 | Trusty et al. |
| 2007/0206275 A1 | 9/2007 | Hemmer et al. |
| 2007/0225550 A1 | 9/2007 | Gattani et al. |
| 2007/0250006 A1 | 10/2007 | Court et al. |
| 2007/0255101 A1 | 11/2007 | Bar-Or |
| 2007/0260121 A1 | 11/2007 | Bakos et al. |
| 2008/0009677 A1 | 1/2008 | Shoroji et al. |
| 2008/0058989 A1 | 3/2008 | Oleynikov et al. |
| 2008/0071140 A1 | 3/2008 | Gattani et al. |
| 2008/0123109 A1* | 5/2008 | Iwasaki .................. G01B 11/25 356/610 |
| 2008/0159653 A1 | 7/2008 | Dunki-Jacobs et al. |
| 2008/0167522 A1 | 7/2008 | Giordano et al. |
| 2008/0167671 A1 | 7/2008 | Giordano et al. |
| 2008/0188716 A1 | 8/2008 | Heckele et al. |
| 2008/0208006 A1 | 8/2008 | Farr |
| 2008/0208041 A1 | 8/2008 | Gilboa |
| 2008/0319311 A1 | 12/2008 | Hamadeh |
| 2009/0017430 A1 | 1/2009 | Muller-daniels et al. |
| 2009/0036744 A1 | 2/2009 | Vayser |
| 2009/0054767 A1 | 2/2009 | Telischak et al. |
| 2009/0192519 A1 | 7/2009 | Omori |
| 2009/0203991 A1 | 8/2009 | Papaioannou et al. |
| 2009/0209998 A1 | 8/2009 | Widmann |
| 2009/0218527 A1 | 9/2009 | French et al. |
| 2009/0225320 A1 | 9/2009 | Bendall et al. |
| 2009/0240111 A1 | 9/2009 | Kessler et al. |
| 2009/0244260 A1 | 10/2009 | Takahashi et al. |
| 2009/0248041 A1 | 10/2009 | Williams et al. |
| 2009/0270682 A1 | 10/2009 | Visser |
| 2009/0318756 A1 | 12/2009 | Fisher et al. |
| 2009/0318758 A1 | 12/2009 | Farr et al. |
| 2009/0318763 A1 | 12/2009 | Koerner et al. |
| 2009/0323053 A1 | 12/2009 | Furman |
| 2010/0036393 A1 | 2/2010 | Unsworth |
| 2010/0065605 A1 | 3/2010 | Shelton et al. |
| 2010/0065609 A1 | 3/2010 | Schwemberger |
| 2010/0069920 A1 | 3/2010 | Naylor et al. |
| 2010/0096435 A1 | 4/2010 | Fuchs et al. |
| 2010/0106015 A1 | 4/2010 | Norris |
| 2010/0200636 A1 | 8/2010 | Zemlok et al. |
| 2010/0228092 A1 | 9/2010 | Ortiz et al. |
| 2010/0268067 A1 | 10/2010 | Razzaque et al. |
| 2011/0043609 A1 | 2/2011 | Choi et al. |
| 2011/0069159 A1 | 3/2011 | Soler et al. |
| 2011/0110114 A1 | 5/2011 | Papac et al. |
| 2011/0112377 A1 | 5/2011 | Papac et al. |
| 2011/0161054 A1 | 6/2011 | Woolf et al. |
| 2011/0165535 A1 | 7/2011 | Berger et al. |
| 2011/0208004 A1 | 8/2011 | Feingold et al. |
| 2011/0237915 A1 | 9/2011 | Yamaguchi |
| 2011/0275901 A1 | 11/2011 | Shelton, IV |
| 2011/0282160 A1 | 11/2011 | Bhadri et al. |
| 2011/0319714 A1 | 12/2011 | Roelle et al. |
| 2012/0024934 A1 | 2/2012 | Shelton et al. |
| 2012/0062724 A1 | 3/2012 | Yokota |
| 2012/0071711 A1 | 3/2012 | Shelton et al. |
| 2012/0071757 A1 | 3/2012 | Salcudean et al. |
| 2012/0082970 A1 | 4/2012 | Pravong et al. |
| 2012/0101497 A1 | 4/2012 | Jayaraj |
| 2012/0108901 A1 | 5/2012 | Sargeant et al. |
| 2012/0116369 A1 | 5/2012 | Viola |
| 2012/0130162 A1 | 5/2012 | Dolt et al. |
| 2012/0143049 A1 | 6/2012 | Neubauer et al. |
| 2012/0184951 A1 | 7/2012 | Viola |
| 2012/0209123 A1 | 8/2012 | King |
| 2012/0238808 A1 | 9/2012 | Teichtmann |
| 2012/0265009 A1 | 10/2012 | Yang et al. |
| 2012/0265010 A1 | 10/2012 | Uram |
| 2012/0265022 A1 | 10/2012 | Menn |
| 2012/0265071 A1 | 10/2012 | Berke |
| 2012/0296163 A1 | 11/2012 | Stopek |
| 2012/0302828 A1 | 11/2012 | Toledo-crow et al. |
| 2013/0023732 A1 | 1/2013 | Kim et al. |
| 2013/0038836 A1 | 2/2013 | Smith |
| 2013/0053782 A1 | 2/2013 | Shelton, IV |
| 2013/0053835 A1 | 2/2013 | Bacher et al. |
| 2013/0060084 A1 | 3/2013 | Fouts et al. |
| 2013/0070070 A1 | 3/2013 | Katakura |
| 2013/0103023 A1 | 4/2013 | Monson et al. |
| 2013/0110005 A1 | 5/2013 | Sharonov |
| 2013/0110006 A1 | 5/2013 | Sharonov et al. |
| 2013/0110129 A1 | 5/2013 | Reid et al. |
| 2013/0123800 A1 | 5/2013 | Leroy et al. |
| 2013/0123801 A1 | 5/2013 | Umasuthan et al. |
| 2013/0144267 A1 | 6/2013 | Chan et al. |
| 2013/0190759 A1 | 7/2013 | Waaler et al. |
| 2013/0197317 A1 | 8/2013 | Daniel et al. |
| 2013/0218024 A1 | 8/2013 | Boctor et al. |
| 2013/0226037 A1 | 8/2013 | Pinto et al. |
| 2013/0226156 A1 | 8/2013 | Sharonov |
| 2013/0267787 A1 | 10/2013 | Warnock |
| 2013/0267975 A1 | 10/2013 | Timm et al. |
| 2013/0281845 A1 | 10/2013 | Luiken |
| 2013/0296712 A1 | 11/2013 | Durvasula |
| 2013/0317351 A1 | 11/2013 | Case et al. |
| 2013/0317352 A1 | 11/2013 | Case et al. |
| 2013/0317353 A1 | 11/2013 | Frank et al. |
| 2013/0324999 A1 | 12/2013 | Price et al. |
| 2013/0345513 A1 | 12/2013 | Tsuruta et al. |
| 2014/0005484 A1 | 1/2014 | Charles |
| 2014/0005682 A1 | 1/2014 | Worrell et al. |
| 2014/0012078 A1 | 1/2014 | Coussa |
| 2014/0012286 A1 | 1/2014 | Lee et al. |
| 2014/0025067 A1 | 1/2014 | Kerr et al. |
| 2014/0030669 A1 | 1/2014 | Hey et al. |
| 2014/0031665 A1 | 1/2014 | Pinto et al. |
| 2014/0046341 A1 | 2/2014 | Dicarlo |
| 2014/0051994 A1 | 2/2014 | Graumann et al. |
| 2014/0052005 A1 | 2/2014 | Yokota |
| 2014/0066784 A1 | 3/2014 | Yokota |
| 2014/0071239 A1 | 3/2014 | Yokota |
| 2014/0071257 A1 | 3/2014 | Yokota |
| 2014/0074116 A1 | 3/2014 | Collins |
| 2014/0088410 A1 | 3/2014 | Wu |
| 2014/0106626 A1 | 4/2014 | Frushour et al. |
| 2014/0107417 A1 | 4/2014 | Mckinley et al. |
| 2014/0107471 A1 | 4/2014 | Haider et al. |
| 2014/0107685 A1 | 4/2014 | O'neill et al. |
| 2014/0114327 A1 | 4/2014 | Boudreaux et al. |
| 2014/0121507 A1 | 5/2014 | Nau, Jr. |
| 2014/0121508 A1 | 5/2014 | Latimer et al. |
| 2014/0148799 A1 | 5/2014 | Mueller |
| 2014/0163359 A1 | 6/2014 | Sholev et al. |
| 2014/0171962 A1 | 6/2014 | Kang |
| 2014/0180001 A1 | 6/2014 | Von Grunberg et al. |
| 2014/0194896 A1 | 7/2014 | Frimer et al. |
| 2014/0200406 A1 | 7/2014 | Bennett et al. |
| 2014/0200561 A1 | 7/2014 | Ingmanson et al. |
| 2014/0204702 A1 | 7/2014 | Ratering |
| 2014/0207002 A1 | 7/2014 | Seow |
| 2014/0235946 A1 | 8/2014 | Smith |
| 2014/0236177 A1 | 8/2014 | Verner et al. |
| 2014/0243658 A1 | 8/2014 | Breisacher et al. |
| 2014/0275764 A1 | 9/2014 | Shen et al. |
| 2014/0275771 A1 | 9/2014 | Henley et al. |
| 2014/0276097 A1 | 9/2014 | Sharonov |
| 2014/0276532 A1 | 9/2014 | Zook et al. |
| 2014/0296636 A1 | 10/2014 | Hatano |
| 2014/0296644 A1 | 10/2014 | Zilberstein et al. |
| 2014/0303491 A1 | 10/2014 | Shekhar et al. |
| 2014/0316206 A1 | 10/2014 | Vasan |
| 2014/0357945 A1 | 12/2014 | Duckworth |
| 2014/0367444 A1 | 12/2014 | Williams |
| 2014/0367591 A1 | 12/2014 | Mahou et al. |
| 2015/0005748 A1 | 1/2015 | Sniffin et al. |

(56) References Cited

U.S. PATENT DOCUMENTS

| | | |
|---|---|---|
| 2015/0018622 A1 | 1/2015 | Tesar et al. |
| 2015/0049907 A1 | 2/2015 | Hong et al. |
| 2015/0065875 A1 | 3/2015 | Friebe |
| 2015/0069108 A1 | 3/2015 | Williams |
| 2015/0073398 A1 | 3/2015 | Toledo-Crow et al. |
| 2015/0076211 A1 | 3/2015 | Irka et al. |
| 2015/0080660 A1 | 3/2015 | Gomez et al. |
| 2015/0080764 A1 | 3/2015 | Poe |
| 2015/0086162 A1 | 3/2015 | Miyahara et al. |
| 2015/0088115 A1 | 3/2015 | Smith |
| 2015/0109427 A1 | 4/2015 | Wood et al. |
| 2015/0119637 A1 | 4/2015 | Alvarez et al. |
| 2015/0133960 A1 | 5/2015 | Lohmeier et al. |
| 2015/0173591 A1 | 6/2015 | Zheng et al. |
| 2015/0230866 A1 | 8/2015 | Tung et al. |
| 2015/0238276 A1 | 8/2015 | Atarot et al. |
| 2015/0265792 A1 | 9/2015 | Goudra et al. |
| 2015/0359418 A1 | 12/2015 | Feussner et al. |
| 2016/0081712 A1 | 3/2016 | Heniford et al. |
| 2016/0166345 A1 | 6/2016 | Kumar et al. |
| 2016/0175057 A1 | 6/2016 | Ibach et al. |
| 2016/0213364 A1 | 7/2016 | Inoue |
| 2016/0270757 A1 | 9/2016 | Toma et al. |
| 2016/0278611 A1 | 9/2016 | Power |
| 2016/0360954 A1 | 12/2016 | Rohling et al. |
| 2017/0055819 A1 | 3/2017 | Hansen et al. |
| 2017/0095269 A1 | 4/2017 | Reid et al. |
| 2017/0105802 A1 | 4/2017 | Taraschi et al. |
| 2017/0172382 A1 | 6/2017 | Nir et al. |
| 2017/0209232 A1 | 7/2017 | Larkin et al. |
| 2017/0238962 A1 | 8/2017 | Hansen et al. |
| 2017/0251900 A1 | 9/2017 | Hansen et al. |
| 2018/0014851 A1 | 1/2018 | Hansen et al. |
| 2018/0042686 A1 | 2/2018 | Peine |
| 2018/0075612 A1 | 3/2018 | Michielin et al. |
| 2018/0325604 A1 | 11/2018 | Atarot et al. |
| 2019/0388161 A1 | 12/2019 | Cicchini et al. |
| 2022/0409298 A1* | 12/2022 | Haider ............. A61B 5/1076 |

FOREIGN PATENT DOCUMENTS

| | | |
|---|---|---|
| CN | 2691487 Y | 4/2005 |
| CN | 1729938 A | 2/2006 |
| CN | 101305901 A | 11/2008 |
| CN | 201316257 Y | 9/2009 |
| CN | 201393995 Y | 2/2010 |
| CN | 201393999 Y | 2/2010 |
| CN | 201602746 U | 10/2010 |
| CN | 101991399 A | 3/2011 |
| CN | 102038480 A | 5/2011 |
| CN | 201861616 U | 6/2011 |
| CN | 102401646 A | 4/2012 |
| CN | 102626301 A | 8/2012 |
| CN | 103299355 A | 9/2013 |
| CN | 203379100 U | 1/2014 |
| CN | 203852327 U | 10/2014 |
| DE | 20002770 U1 | 10/2000 |
| DE | 102004008488 A1 | 9/2004 |
| DE | 102005045706 B3 | 4/2007 |
| DE | 102007007742 A1 | 8/2008 |
| DE | 102008056830 A1 | 5/2010 |
| DE | 202011103007 U1 | 11/2011 |
| DE | 102012209448 A1 | 12/2013 |
| DE | 102012209450 A1 | 12/2013 |
| EP | 2412290 A1 | 2/2012 |
| EP | 1961372 B1 | 3/2012 |
| EP | 2554103 A1 | 2/2013 |
| EP | 2630915 A1 | 8/2013 |
| EP | 2551698 B1 | 9/2014 |
| EP | 3056934 A1 | 8/2016 |
| FR | 2851701 A1 | 8/2004 |
| JP | 2000131623 A | 5/2000 |
| JP | 2001025469 A | 1/2001 |
| JP | 2003061970 A | 3/2003 |
| JP | 2006271600 A | 10/2006 |
| JP | 2015073663 A | 4/2015 |
| WO | 9510218 A1 | 4/1995 |
| WO | 0042906 A2 | 7/2000 |
| WO | 0152720 A1 | 7/2001 |
| WO | 02080773 A1 | 10/2002 |
| WO | 2005122940 A1 | 12/2005 |
| WO | 2009116969 A1 | 9/2009 |
| WO | 2009134634 A2 | 11/2009 |
| WO | 2012072112 A1 | 6/2012 |
| WO | 2012083247 A1 | 6/2012 |
| WO | 2013002050 A1 | 1/2013 |
| WO | 2013096896 A1 | 6/2013 |
| WO | 2013163391 A1 | 10/2013 |
| WO | 2014140813 A1 | 9/2014 |
| WO | 2014174726 A1 | 10/2014 |
| WO | 2014198675 A1 | 12/2014 |
| WO | 2015124159 A1 | 8/2015 |
| WO | 2015133958 A1 | 9/2015 |
| WO | 2015135055 A1 | 9/2015 |
| WO | 2015149041 A1 | 10/2015 |
| WO | 2016018815 A1 | 2/2016 |
| WO | 2016019424 A1 | 2/2016 |
| WO | 2016057989 A2 | 4/2016 |

OTHER PUBLICATIONS

U.S. Appl. No. 15/120,256, filed Aug. 19, 2016, Set Comprising a Surgical Instrument.

U.S. Appl. No. 15/589,476, filed May 8, 2017, Cannula Assembly Kit.

U.S. Appl. No. 15/601,276, filed May 22, 2017, Real Time Correlated Depiction System of Surgical Tool.

U.S. Appl. No. 17/330,949, filed May 26, 2021, Real Time Correlated Depiction System of Surgical Tool.

U.S. Appl. No. 17/320,417, filed May 14, 2021, Minimally Invasive Surgery System.

Extended European Search Report received for European Patent Application No. 17169285.8, mailed on Aug. 31, 2017, 7 pages.

Extended European Search Report received for European Patent Application No. 17884041.9, mailed on Aug. 12, 2020, 11 pages.

Supplementary European Search Report received for European Patent Application No. 16781653.7, mailed on May 22, 2017, 4 pages.

Supplementary European Search Report received for European Patent Application No. 16853132.5, dated Oct. 27, 2017, 4 pages.

Ackerman et al. (2002) "Surface Reconstruction of Abdominal Organs Using Laparoscopic Structured Light for Augmented Reality", Proceedings of SPIE, 4661:39-46.

Albitar et al. (Oct. 14-21, 2007) "Robust Structured Light Coding for 3D Reconstruction", Proceedings of the 2007 IEEE 11th International Conference on Computer Vision, 6 pages.

Bauer et al. (2013) "Real-Time Range Imaging in Health Care: A Survey" Time-of-Flight and Depth Imaging. Sensors, Algorithms, and Applications. Dagstuhl Seminar 2012 and GCPR Workshop on Imaging New Modalities, Lecture Notes in Computer Science, 8200:188-212.

Choi et al. (May 5, 2015) "An Effective Visualization Technique for Depth Perception in Augmented Reality-based Surgical Navigation", International Journal of Medical Robotics and Computer Assisted Surgery, 12(1):11 pages.

Clancy et al. (2011) "Spectrally Encoded Fiber-based Structured Lighting Probe for Intraoperative 3D Imaging", Biomedical Optics Express, 2(11):3119-3128.

Edgcumbe et al. (Sep. 14-18, 2014) "Pico Lantern: A Pick-up Projector for Augmented Reality in Laparoscopic Surgery", Medical Image Computing and Computer-Assisted Intervention (MIC-CAI) 17th International Conference, 432-439.

Geng et al. (2011) "Structured-light 3D Surface Imaging: A Tutorial", Advances in Optics and Photonics, 3:128-160.

Hao Wei (Dec. 2011) "Wide Baseline Stereo Image Rectification and Matching", Dissertation. The University of Tennessee, 176 pages.

(56) References Cited

OTHER PUBLICATIONS

Kang Hyosig (May 2002) "Robotic Assisted Suturing In Minimally Invasive Surgery", Thesis. Rensselaer Polytechnic Institute, 183 pages.

Karjee et al. (Jul. 3-4, 2014) "Spatial Data Estimation in Three Dimensional Distributed Wireless Sensor Networks", International Conference on Embedded Systems, 139-144.

Krupa et al. (May 11-15, 2002) "Autonomous Retrieval and Positioning of Surgical Instruments in Robotized Laparoscopic Surgery Using Visual Servoing and Laser Pointers", Proceedings of the 2002 IEEE International Conference on Robotics and Automation, 4:3769-3774.

Louw et al. (2005) "An approximate EM Homographical Iterative Closest Point algorithm", PRASA2005, Langebaan, 89-92.

Maier-Hein et al. (Oct. 2014) "Comparative Validation of Single-shot Optical Techniques for Laparoscopic 30 Surface Reconstruction", IEEE Transactions on Medical Imaging, 33(10):1913-1930.

Maier-Hein et al. (2013) "Optical Techniques for 30 Surface Reconstruction in Computer-assisted Laparoscopic Surgery", Medical Image Analysis, 17(8):974-996.

Maurice et al. (2013) "Real-time Structured Light Coding for Adaptive Patterns", J. Real-Time Image Proc, 8:169-178.

Nicolau et al. (Sep. 2011) "Augmented Reality in Laparoscopic Surgical Oncology", Surgical Oncology, 20(3):189-201.

International Search Report and Written Opinion received for PCT/DK2016/050180, mailed on Apr. 11, 2016, 18 pages.

Pellicano et al. (Dec. 4-8, 2016) "Robust Wide Baseline Pose Estimation from Video (Supplementary Material)", Proceedings of the International Conference on Pattern Recognition (ICPR), 2 pages.

Pennington et al. (Jul. 2001) "Miniaturized 3-D Surface Profilometer using a Fiber Optic Coupler", Optics & Laser Technology, 33(5):313-320.

Pritchett et al. (Jan. 4-7, 1998) "Wide Baseline Stereo Matching", Proceedings of the Sixth International Conference on Computer Vision, 754-760.

Reiter et al. (2014) "Surgical Structured Light for 3D Minimally Invasive Surgical Imaging", Proceedings of the IEEE/RSJ International Conference on Intelligent Robots and Systems, 1282-1287.

Salvi et al. (Apr. 2004) "Pattern Codification Strategies in Structure Light Systems", Pattern Recognition, 37(4):827-849.

Schick et al. (May 26, 2011) "3D Measuring in the Field of Endoscopy", Proceedings of SPIE, 8082:808216-1-808216-12.

Schmalz et al. (2012) "An endoscopic 30 scanner based on structured light", Medical Image Analysis, 16:1063-1072.

Su et al. (Aug. 26, 2015) "Three-dimensional Shape Measurements using Endoscopes", Proceedings of SPIE, 9586:95861H-1-95861H-6.

Zhang et al. (Sep. 1, 2010) "A Surface Topology and Motion Compensation System for Microsurgery Guidance and Intervention based on Common-Path Optical Coherence Tomography", IEEE Trans Biomed Eng, 56(9):2318-2321.

* cited by examiner

SET COMPRISING A SURGICAL INSTRUMENT

CROSS-REFERENCE TO RELATED APPLICATIONS

The present application is a continuation of U.S. patent application Ser. No. 15/120,256 entitled "Set Comprising a Surgical Instrument" filed Aug. 19, 2016, which is national stage application of PCT/DK2015/050035 entitled "Set Comprising a Surgical Instrument" with an international filing date of Feb. 2, 2015, which further claims priority to Danish Application No. PA 2014 70716, filed Nov. 20, 2014 and European Patent Application No. 14156155.5, filed Feb. 21, 2014, all of which are incorporated herein by reference.

TECHNICAL FIELD

The invention relates to a set comprising a surgical instrument suitable for use in a minimal invasive surgery and/or for training the handling of such surgical instrument as well as a surgical system, a training kit, a method of training and performing minimal invasive surgery.

BACKGROUND ART

Minimal invasive surgery has been used increasingly in the last years due to the benefits compared to conventional open surgery as it reduces the trauma to the patient tissue, leaves smaller scars, minimizes post-surgical pain and enables a faster recovery of the patient.

For example, in laparoscopic surgery (a form of minimal invasive surgery) the surgeon accesses a body cavity, such as the abdominal or pelvic cavity, through a series of small incisions. A laparoscope is inserted through an incision, and conventionally connected to a monitor, enabling the surgeon to see the inside of the abdominal or pelvic cavity. In order to perform the surgery procedure, surgical instruments are inserted through incisions. In addition, the body cavity around the surgical site is inflated with a fluid, preferably gas e.g. carbon dioxide in order to create an 'air' space within the cavity for the surgeon to view the surgical site and move the laparoscopic instruments.

In conventional open surgery the surgeon can use the normal visual-motor relations, wherein the motor control is based on visual perception, such that a desired movement of a surgical instrument can be performed on basis of vision. In other words, during conventional open surgery the normal link between the visual perception and the motor system is conserved. However, when performing minimal invasive surgery the surgeon has an indirect vision of the surgical field which results in dissociation of the visual perception and the motor system of the surgeon. Consequently, the surgeon needs to acquire new skills in order to correctly connect his or hers visual perception and motor system (hand-eye coordination) during minimal invasive surgery.

Visual perception is the ability to interpret the surrounding environment by processing information obtained by use of the eyes, in the present case the surrounding environment can be the inside of a body cavity, such as the abdominal or pelvic cavity.

The motor system of a person is the complex system which, among other things, controls voluntary movements, enabling a surgeon to move body parts, such as a hand and fingers, to control the movement of a surgical instrument inside a body cavity.

Further, the remote vision of the surgical field is normally displayed on a monitor in two dimensions whereas the surgical instrument is manipulated in three dimensions: this results in a poor spatial and depth perception which makes it even harder for a surgeon to acquire the new abilities for connecting visual perception of the remote vision (in two-dimensions) and motor system moving the surgical tools (in three-dimensions).

In addition, if the surgical tools are controlled via a surgical robot the normal three dimensional motor behaviors of the surgeon are processed and changed by the robot, which makes it more difficult for the surgeon to correctly connect his or hers visual perception and motor system during minimal invasive surgery.

Training in minimal invasive surgery is normally performed after basic surgical training and is based on apprenticeship where the skills are obtained in direct clinical surgery supervised by an experienced surgeon. This training method poses considerable risk to the patient and requires a substantially amount of time from the experienced surgeon.

Therefore, the use of simulators, for example laparoscopic simulators, is preferred in order for an inexperienced surgeon to learn the basic skills before starting to do clinical surgery. Among the most important skills needed to master is: the ability to transform the information received by indirect vision into a three dimensional understanding.

Different approaches for providing an improved depth perception have been provided for example as described in EP 2630915 in which a light instrument for use in minimal invasive surgery is described. The light instrument includes an elongate tubular member and a metrology system mounted on the elongate tubular member. The metrology system includes a mask, a zoom lens assembly and a light element arranged such that the light element propagates light beams through the mask and the zoom lens assembly to project the patterns of the mask onto the surgical site of interest to provide markings as references used for measuring by the surgeon.

US 2013/0296712 describes an apparatus for determining endoscopic dimensional measurements, including a light source for projecting light patterns on a surgical sight including shapes with actual dimensional measurements and fiducials, and means for analyzing the projecting light patterns on the surgical sight by comparing the actual dimensional measurements of the projected light patterns to the surgical site.

WO 2013/163391 describes at system for generating an image which the surgeon can use for measure the size of or distance between structures in the surgical field by using an invisible light for marking a pattern to the surgical field.

The system comprises a first camera: a second camera: a light source producing light at a frequency invisible to a human eye: a dispersion unit projecting a predetermined pattern of light from the invisible light source: an instrument projecting the predetermined pattern of invisible light onto a target area: a band pass filter directing visible light to the first camera and the predetermined pattern of invisible light to the second camera: wherein the second camera images the target area and predetermined pattern of invisible light, and computes a three-dimensional image.

DISCLOSURE OF INVENTION

The object of the present invention is to provide a tool comprising a surgical instrument suitable for use in minimal invasive surgery and/or for training the handling of such surgical instrument, which tool provides the surgeon with good visual perception for handling the surgical instrument and preferably with enhanced visual perception when performing the surgery and which tool simultaneously is relatively simple to use and can be produced at adequate cost.

It is also an object to provide a method for performing minimal invasive surgery and/or training therefor which method provides the surgeon with good visual perception.

These and other objects have been solved by the invention or embodiments thereof as defined in the claims and as described herein below.

It has been found that the invention or embodiments thereof have a number of additional advantages which will be clear to the skilled person from the following description.

The tool is provided in form of a correlated set for minimal invasive surgery comprising a surgical instrument and a pattern generating member which can be assembled as described below to form a surgical instrument assembly.

In an embodiment of the present invention a surgical instrument assembly for use in minimal invasive surgery which enhances the surgeon's visual perception such that the surgeon is able to connect his or hers visual perception and motor system during minimal invasive surgery whereby an intended movement of the surgical instrument can be performed on basis of remote vision.

The correlated set for minimal invasive surgery comprises a surgical instrument and a pattern generating member. The surgical instrument has a distal end and a proximal end and comprises a handle portion at its proximal end, a surgical tool at its distal end and a body portion connecting the handle portion to the surgical tool. The pattern generating member comprises a pattern light source and a projector. The pattern light source is operatively connected to the projector for projecting a light pattern. At least the projector of the pattern generating member is configured for being at least temporarily fixed to the body portion of the surgical instrument such that a movement of the surgical tool results in a correlated movement of the projector.

Thereby, when the tool is moved, the projector will move in a correlated way which results in that the projected pattern as seen on a distally arranged surface will change accordingly. This change of the projected pattern in response to a surgeons' movement of the tool provides the surgeon with a very good visual perception of the 3D space in which the surgical tool is moved and thereby it will be simpler for the surgeon to handle the surgical tool with high accuracy. Further the surgeon needs less time to orientate in the 3D space which also makes it possibly to perform the surgical procedure relatively fast.

The terms distal and proximal should be interpreted in relation to the orientation of the surgical instrument.

The phrase "distal direction" means a direction with a vector oriented from the proximal end to the distal end of the surgical instrument.

The phrase "proximal direction" means a direction with a vector oriented from the distal end towards the proximal end of the surgical instrument.

The distal and proximal directions are determined when the body portion of the surgical instrument is in straight position.

Any planes and angles to the distal and proximal directions are all well determined when the body portion of the surgical instrument is in straight position.

The body portion of the surgical instrument has a longitudinal axis determined in straight position which longitudinal axis is parallel to the distal and proximal directions.

The phrase "distal to" means "arranged at a position in distal direction to". The phrase "distally arranged" means arranged distal to the distal end of the surgical instrument.

The term "surgical instrument assembly" means an assembly comprising the surgical instrument and pattern generating member.

The term "substantially" should herein be taken to mean that ordinary product variances and tolerances are comprised.

The term "about" is generally used to ensure that what is within measurement uncertainties are include. The term "about" when used in ranges, should herein be taken to mean that what is within measurement uncertainties are included in the range.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

Throughout the description or claims, the singular encompasses the plural unless otherwise specified or required by the context.

In an embodiment the surgical instrument for use in minimal invasive surgery where a surgeon performs a surgical procedure within a body cavity with indirect vision of a surgical field comprises, a handle portion for manipulation of the instrument, and a body portion extending from the handle portion and comprising a surgical tool, wherein the body portion is adapted to be inserted through an incision in a body into the body cavity. The pattern generating member is fixed to the body portion and when the body part is inserted into the body cavity, it projects a light pattern on an area of the surgical field such that the contours of the surgical field and the position of the instrument can be deduced by the surgeon based on indirect vision of the light pattern.

Thus, it is possible for the surgeon to use the light pattern as a reference in order to connect the remote vision with the movement of the surgical tools. The light pattern can be interpreted as a monocular reference which enables the surgeon to determine the position of the surgical instrument and the contours of the surgical field. Consequently, the present invention enables the surgeon to overcome the difficulties in connecting his or hers visual perception and motor system during minimal invasive surgery.

In an embodiment the indirect vision of the surgical field can be obtained through an endoscope inserted through an incision in the body. The endoscope is advantageously connected to a monitor for displaying the surgical field in a two dimensions image.

The handle portion can comprise an actual handle for the surgeon to seize and thereby control the surgical instrument directly. In another embodiment, the handle portion is controlled by use of an actuator connected to a control mechanism, for example a surgical robot, such that the surgeon can control the surgical instrument indirectly.

The invention also comprises the correlated set in assembled condition i.e. the surgical instrument assembly.

The surgical instrument assembly mentioned above can both be used in training of surgeons in minimal invasive surgery and during an actual surgical procedure. When used during training it will reduce the training time before a minimal invasive surgeon is sufficiently skilled to perform live surgery.

Light pattern can for example be a grid or a plurality of light dots that generate the pattern. In an embodiment the light pattern comprises one or more cones of light that forms a geometric shape, such as a square. The surgeon can then use the curves defined by the edges of the geometric shape to determine the position of the surgical instrument and the contours of the surgical field.

When used during the actual surgical procedure it will help the surgeon, hereby minimizing the risk of mistakes and secure a smoother surgical procedure.

Advantageously the projector of the pattern generating member is configured for being at least temporarily fixed to the body portion of the surgical instrument such that at least any non-rotational movement of the surgical tool results in a correlated movement of the projector.

The phrase "rotational movement of the surgical tool" is a movement that is exclusively rotational with a rotation axis coincident with an axis of the body portion of the surgical tool when the body portion of the surgical instrument is straight. Any other movements of the surgical tool are non-rotational movements.

It has been found that some surgeons may in certain situations be distracted in case a mere rotational movement of the surgical tool results in a correlated movement of the projector and thereby the projected pattern.

In an embodiment the projector or the shape of the pattern is configured such that a mere rotational movement of the surgical tool does not result in a correlated movement of the projector and thereby the projected pattern.

In an embodiment the projector of the pattern generating member is configured for being at least temporarily fixed to the body portion of the surgical instrument such that any non-rotational movement of the surgical tool results in a correlated movement of the projector. Thereby a very improved visual perception in 3D can be obtained which ensures that the surgeon can handle the surgical instrument assembly with high precision. Advantageously the fixation of the pattern generating member is configured for being controllable by the surgeon, such that the surgeon can switch on and off movement of the generated pattern in response to rotational movement of the surgical instrument. In an embodiment at least the projector of the pattern generating member is configured for being at least temporarily fixed to the body portion of the surgical instrument using a fixing element comprising a rotation element, such as a turntable or a rotation disc allowing at least partially rotation of the projector, wherein the fixing element preferably comprising a switch for blocking rotation of the rotation element.

The projector of the pattern generating member or the whole pattern generating member is adapted for being temporarily or permanently fixed to the body portion of the surgical instrument. The phrase "temporarily fixed" is used to mean that the projector or the whole pattern generating member can be dissembled from the surgical instrument after use, e.g. for cleaning for reuse.

By having the surgical instrument and the pattern generating member with the projector as separate units e.g. for assembling by the user, the user can for example have a correlated set with several different pattern generating members to choose between, thereby allowing the surgeon to select which pattern generating member he/she wishes to use for a specific procedure.

Further it also allows a simpler production because the surgical instrument and the pattern generating member of the correlated set may be produced and sold separately.

In an embodiment the pattern generating member is detachably attached to the body portion. The surgeon can then remove the pattern generating member if needed. In addition, the pattern generating member can be attached to an existing surgical instrument in order to obtain a surgical instrument assembly.

The projector or the whole pattern generating member can be attachable to the body portion of the surgical instrument by any suitable means which provides a sufficiently safe attachment. The projector or the whole pattern generating member may for example be temporarily or permanently fixed to the surgical instrument by a click lock, a sleeve lock, a screw lock, a turn lock, a wedge lock or combinations thereof.

By providing the pattern generating member as a detachable unit, the pattern generating member or for example the projector of the pattern generating member can be replaced whenever desired. Further, it has been found that it is simpler to clean the surgical instrument for reuse without the pattern generating member or parts thereof. In an embodiment the pattern generating member is a disposable unit. In an embodiment the projector is a disposal unit.

The pattern generating member may be selected by the surgeon for the specific surgery—i.e. different pattern may be preferred in different surgeries, such as different shape of pattern, different size of pattern and/or different wavelength(s).

In an embodiment at least the projector of the pattern generating member is temporarily fixed to the body portion of the surgical instrument by a sleeve which surrounds the body portion in at least a length section thereof of the surgical instrument. The sleeve may simultaneously hold and protect the optical fiber. The sleeve may in principle be of any material. Where the surgical instrument assembly is for use in training there is no specific requirements to the sleeve material, however generally it is desired that the sleeve is of a relatively light material e.g. with a density below 1 $g/cm^3$, such as of about 0.97 $g/cm^3$ or less. Preferably the sleeve is of polymer material or a composite material. For application in surgery the sleeve material is preferably an olefin polymer, polyurethane or silicone. The sleeve preferably has a low-friction outer surface in order to reduce friction between the sleeve and tissue during surgery.

In an embodiment the sleeve comprises a low friction coating e.g. of PTFE or a hydrophilic material e.g. a coating comprising hydrogel (e.g. based on alkyl methacrylate) and/or polyvinylpyrridine.

The sleeve is preferably arranged to fit tight around the body—i.e. the inner diameter of the sleeve is approximately as or slightly larger than the body.

The thickness of the sleeve material surrounding the body—here referred to as the sleeve wall—may be any thickness taken into account that the surgery instrument assembly should not be too bulky in particular the part of the sleeve that is adapted to be inserted through an incision and/or through a hole in the cover of a training kit. The thickness of the sleeve wall may vary along the length of the body and/or in its annular or semi-annular extension around the body. Examples of suitable sleeve wall thickness are from about 0.1 to about 10 mm, such as from about 2-5 mm.

In an embodiment the sleeve comprises two or more layers of equal or different materials.

In an embodiment the sleeve comprises a first elongate through hole for the body and a separate elongate hole for the optical fiber, such that the sleeve provide a protection cover for the optical fiber from the end of the sleeve closest to the handle when mounted and to the projector. The sleeve may comprise additional through holes and/or pockets e.g. for other elements of the pattern generation member e.g.

such that further parts e.g. All parts of the pattern generating member can be fixed to the surgical instrument e.g. to the body of the surgical instrument by the sleeve. Thereby it becomes even simpler to mount the pattern generation member.

The outer diameter of the sleeve, in particular the part of the sleeve that is adapted to be inserted through an incision, is advantageously about 15 mm or less, such as about 10 mm or less. For certain applications the outer diameter may be larger.

In an embodiment the projector of the pattern generating member is temporarily fixed to the body portion of the surgical instrument by a sleeve where the sleeve comprises a fixing element arranged immediately adjacent to the handle. The fixing element advantageously comprises a rotation element such as described above.

In embodiments where only the pattern light source is not fixed or adapted to be fixed to the surgical instrument it is desired that the optical fiber guiding the light to the projector can be arranged on either side of the handle selected by the surgeon and e.g. in a fixed position in order not to bother the surgeon during surgery.

In an embodiment at least the projector and the pattern light source of the pattern generating member are temporarily fixed to the body portion of the surgical instrument by a sleeve.

In an embodiment all elements of the pattern generating member are temporarily fixed to the body portion of the surgical instrument by a sleeve. The elements of the pattern generating member comprises the projector and the pattern light source and optional power source and/or one or more controlling elements such as the pattern light source control unit described below.

In an embodiment at least the projector of the pattern generating member is permanently fixed to the surgical instrument, preferably the pattern generating member is integrated with the surgical instrument to form an integrated surgical instrument assembly.

In an embodiment the pattern generating member including the pattern light source and an optional battery is incorporated into the body of the surgical instrument.

Advantageously the correlated movement between the surgical tool and the projector is such that a given movement of the surgical tool results in a given predetermined movement of the projector.

The surgical instrument can in principle be any kind of surgical instrument for minimal invasive surgery. The term "surgical instrument" is herein used to denote an instrument which is for performing the actual invasive act contrary to instruments for illumination or acquiring images and similar not invasive instruments.

In an embodiment the surgical instrument is a laparoscopic instrument, an arthroscopic instrument and/or a thoracoscopic instrument, a gastroscopic instrument, a colonoscopic instrument, a laryngoscopic instrument, a broncoscopic instrument, a cytoscopic instrument or a combination thereof.

In an embodiment the surgical instrument has a rigid body portion and advantageously the body portion of the surgical instrument provides a rigid interconnection between the handle portion and the surgical tool. For example the body portion is rigid and the body portion preferably has length extending from the handle portion to the surgical tool. The body portion is preferably straight along its length. Such substantially rigid surgical instrument advantageously is a laparoscopic instrument, an arthroscopic instrument and/or a thoracoscopic instrument.

A laparoscopic instrument is usually applied for minimal invasive surgery in the abdomen. An arthroscopic instrument is usually applied for minimal invasive surgery at or inside of a joint. A thoracoscopic instrument is usually applied for minimal invasive surgery in the chest (heart, lungs, great vessels).

In an embodiment the surgical instrument is an endoscopic surgical instrument for use together with an endoscope where the surgical instrument is arranged in a channel in the endoscope during the surgical procedure. Such surgical instruments are in particular suitable in gastroscopy, colonoscopy, laryngoscopy, broncoscopy and cystoscopy and advantageously such surgical instrument has a flexible body portion. In an embodiment the body portion of the surgical instrument provides a flexible interconnection between the handle portion and the surgical tool.

In general the surgical instrument for minimal invasive surgery are relatively similar, however often they differs in size in relation to their purpose, i.e. whether it is a laparoscopic instrument, an arthroscopic instrument and/or a thoracoscopic instrument. Further as explained above the body portion of surgical instrument may be rigid or flexible.

The body portion of the surgical instrument can in principle have any length depending on the surgery to be performed e.g. from a few cm, such as 5 cm to about 50 cm or even up to about 200 cm. Generally, flexible surgical instrument will have longer body portions than rigid surgical instrument. The length of the body portion is determined from the handle portion to the surgical tool. In an embodiment the body portion has a length of from about 35 cm to about 40 cm.

Advantageously the surgical tool is adapted to perform a surgical intervention at a surgery target site. In an embodiment the surgical tool is selected from a grasper, a suture grasper, a stapler, forceps, a dissector, scissors, a suction instrument, a clamp instrument, an electrode, a curette, ablators, scalpels, a needle holders, a biopsy and retractor instrument or a combination thereof.

All of such surgical tools are well known to a skilled person and will not be described in further details. The surgical tool is advantageously adapted to be operating in direct contact with the tissue. Such instruments require to be controlled with a very high precision and accordingly the invention provides a very valuable contribution for improving the control and operation of the surgical instrument in proximal directions for high precision minimal invasive surgery.

The pattern light source can in principle be any kind of light source capable of providing a desired pattern. The light source may be a coherent light source or an incoherent light source.

The term "coherent light" is herein used to denote laser light whereas "incoherent light" includes any non-laser lights irrespectively of its Degree of coherence. Incoherent light with a relatively high degree of coherence (sometimes called partially coherent light) are often preferred because the incoherent light provides a sufficient bright pattern, while the incoherent light source generally can be obtained a much lower cost than coherent light.

In an embodiment the pattern light source is a coherent light source, such as a semiconductor light source, such as a laser diode and/or a VCSEL light source.

In an embodiment the pattern light source is an incoherent light source, preferably the light source is a semiconductor light source, such as a light emitting diode (LED).

Advantageously, the light pattern is generated by at least one laser and/or LED. Lasers and LED's (light emitting diodes) are advantageous as they can generate light patterns that are well defined and it is possible to choose the wavelength, and thus color, such that the pattern is enhanced in the remote vision. For example such that the light pattern is clearly visible and enhanced on the monitor.

The pattern light source advantageously has a relatively narrow band width thereby providing a bright light in the narrow bandwidth, while simultaneously emitting a relatively low light energy. This is advantageously both to avoid undesired heating of the surgical target site and simultaneously have low risk of blinding the surgeon.

In an embodiment the pattern light source has a band width (full width at half maximum—FWHM) of up to about 50 nm, such as from 1 nm to about 40 nm. Preferably the narrow band width of the pattern light source is about 25 nm or less, such as about 10 nm or less.

In an embodiment the pattern light source has a center wavelength of about 450 nm to about 600 nm, such as about 532 nm.

In an embodiment the pattern light source has a red center wavelength within the range 610 nm<$\lambda$<760 nm.

In an embodiment the pattern light source has an orange center wavelength within the range 590 nm<$\lambda$<610 nm.

In an embodiment the pattern light source has a yellow center wavelength within the range 570 nm<$\lambda$<590 nm.

In an embodiment the pattern light source has a green center wavelength within the range 500 nm<$\lambda$<570 nm.

In an embodiment the pattern light source has a blue center wavelength within the range 450 nm<$\lambda$<500 nm.

In principle the pattern light source can comprise any wavelengths such as wavelengths within visible light or within invisible light. Where the light is invisibly the light pattern is adapted to be read by a detector capable of detecting the light wavelength in question. The detector may for example be part of a computer connected to a monitor for showing the pattern and/or the detector may be part of a robot as further described below.

In an embodiment the pattern light source has a band width comprising visible light having wavelength in the range from about 400 nm to about 900 nm, preferably in the range from about 450 nm to about 700 nm, preferably in the range from about 500 nm to about 650 nm.

In an embodiment the pattern light source has a band width comprising invisible light, such as light having wavelength above about 900 nm and/or below about 450 nm.

In an embodiment pattern generating member comprises two or more pattern light sources having equal or different bandwidths, wherein the two or more pattern light sources preferably are operatively connected to the projector.

the two or more pattern light sources can be operated independent of each other i.e. they can independently be switched on and off e.g. using a non-hand held unit or by a unit incorporated into the handle of the surgical instrument.

In an embodiment—the two or more pattern light sources can be connected to separate projectors.

Generally it is desired that the pattern light source (or sources) can be switched on and off and optionally be modified in wavelength and/or intensity, using a pattern light source control unit. In an embodiment the pattern light source control unit is a non-hand held unit, such as a pedal or a voice activated control unit—thereby the surgeon can in a simple manner control the light pattern. In an embodiment the pattern light source control unit is incorporated into the handle of the surgical instrument for simple handling by the surgeon.

Advantageously the pattern light source is arranged to provide a pattern output power which is sufficient to generate a visible pattern, but not too high such that an undesired amount of heat may be generated. Preferably the pattern light source is arranged to provide a pattern output power up to about 5 mW such as from about 0.1 to about 4 mW, such as from about 0.5 to about 1.5 mW. Preferably the pattern output power is adjustable. The pattern output power is determined as the output power of the projector.

The projector of the pattern generating member is adapted to project a pattern.

Advantageously the projector of the pattern generating member comprises a phase optic element, a spatial light modulator, a multi-order diffractive lens, a holographic lens, a Fresnel lens and/or a computer regulated optical element.

The phase optic element may advantageously be a diffractive optic element (DOE).

In an embodiment the phase optics element is capable of producing an image having periodic intensity distribution.

Diffractive optic elements are well known in the art and may for example utilize a surface with a complex microstructure for its optical function. The micro-structured surface relief profile has two or more surface levels. The surface structures are either etched in fused silica or other glass types, or embossed in various polymer materials. Additionally, diffractive optics can realize almost the same optical functions as refractive optics such as lenses, prisms or aspheres, but they are much smaller and lighter. DOEs are not limited to laser applications; partially coherent light from LEDs or other light sources can also be modulated.

In an embodiment the DOE is as described in US 2013/0038836 e.g. as shown in FIG. 1 and/or as described in section [015] of US 2013/0038836.

In an embodiment the diffractive optic elements comprises a "multi-order diffractive" lens, such as a conventional diffractive-optic lens utilizing a single diffraction order in which the optical power of the lens is directly proportional to the wavelength of light.

The projector may comprise any type of beam manipulating element for providing the desired pattern e.g. lenses and/or mirrors and/or splitters and/or filters and/or collimator.

In an embodiment the projector comprises a spatial light modulator. The spatial light modulator configured for modulating the light pattern for example by modulating the transparency of a pattern cover e.g. by a computer modulation. In an embodiment the spatial light modulator is arranged for modulating the intensity and/or the phase of the light from the pattern light source to thereby modulate the emitted light pattern.

In order to ensure that the minimal invasive surgery can be performed with a desired small incision it is generally desired that the part of the pattern generating member to be mounted to the body portion of the surgical instrument is relatively small.

Advantageously the projector of the pattern generating member has a maximal extending area perpendicular to the proximal direction when the pattern generating member is fixed to the body portion of the surgical instrument and the body portion is in straight position, which maximal extending area is up to about 4 cm$^2$, such as up to about 2 cm$^2$, such as from about 0.01 to about 1 cm$^2$, such as from about 0.1 to about 0.5 cm$^2$.

Where the whole pattern generating member is to be fixed to the body portion of the surgical instrument it is desired that the whole pattern generating member has a maximal extending area perpendicular to the proximal direction when the pattern generating member is fixed to the body portion of the surgical instrument and the body portion is in straight position, which maximal extending area is up to about 4 cm$^2$, such as up to about 2 cm$^2$, such as from about 0.01 to about 1 cm$^2$, such as from about 0.1 to about 0.5 cm$^2$.

The pattern light source is operatively connected to the projector to transfer light to the projector. The operatively connection can in principle be any kind of wave guiding element or elements, such as an optical fiber, one or more lenses, mirrors, splitters, collimators, amplifiers or any other suitable optical element.

In an embodiment, the light source is not intended to be inserted into the body cavity and the operatively connection e.g. at least one optical waveguide is adapted to guide the light from the pattern light source through the incision in the body to the projector. Thus, the projector of the pattern generating member that is inserted in to the body cavity can be made relatively small, as the light can be generated outside the body cavity and guided via optical waveguides to the body cavity where it can be projected onto the area of the surgical field. Advantageously, the pattern light source can be detached from the at least one optical waveguide. This simplifies the sterilization process of the surgical instrument as the pattern light source does not need to be sterilized in case it does not enter the body cavity. In an example, there is one pattern light source that is either connected to one optical waveguide or a plurality of optical waveguides. In another example, there are more than one pattern light source.

In an embodiment the pattern light source is adapted for being arranged at a distance to the projector, e.g. such that it need not be inserted through the incision in use. The pattern light source is in an embodiment incorporated into a pattern light source housing arranged to be positioned at a distance to the surgical instrument and advantageously connected to the projector via connection means comprising an optical fiber. Preferably the optical fiber is protected by a polymer cover.

In an embodiment the pattern light source is (or is adapted for being) connected to or incorporated into the handle of the surgical instrument. In this embodiment the pattern light source control unit as discussed above is advantageously also (or is adapted for being) connected to or incorporated into the handle of the surgical instrument.

The pattern generating member is connected or adapted to be connected to a power source. In an embodiment the power source is a battery.

The pattern light source and/or optional battery is/are in an embodiment incorporated into or fixed to the body of the surgical instrument. Advantageously the pattern light source is fixed to or incorporated into the handle of the of the surgical instrument and the battery is incorporated into or fixed to the body of the surgical instrument, preferably near the proximal end of the surgical instrument, such as closest to the handle than to the surgical tool.

In an embodiment the pattern light source and the battery are incorporated into a pattern light source housing which is adapted to be arranged external during a surgery e.g. in the handle of the surgical instrument as described above.

In an embodiment where the pattern light source and the battery are incorporated into a pattern light source housing, the pattern light source housing is incorporated into or fixed to the body of the surgical instrument, preferably near the proximal end of the surgical instrument, such as closest to the handle than to the surgical tool.

In an embodiment the pattern light source and the battery are incorporated into a pattern light source housing together with the projector to form the pattern generating member which is adapted to be mounted to the body portion of the surgical instrument.

In an embodiment the pattern light source and optionally the pattern light source control unit is/are adapted for being or is/are connected to or incorporated into the handle of the surgical instrument and the pattern light source is connected to an external battery arranged at a distance from the surgical instrument.

In an embodiment the pattern light source and/or a power source or a power input connector is/are fixed to the body of the surgical instrument using a sleeve as described above. In this embodiment preferably also other elements such as the projector and optional control units are fixed to the body of the surgical instrument using the sleeve.

In an embodiment the projector pattern light source, the power source in form of one or more batteries or a power input connector, the projector and a control unit as described above are fixed to the body of the surgical instrument using the sleeve. One or more, such as all of the pattern light source, the power source, the projector and the control unit is/are advantageously fixed (temporally or permanently fixed) to the sleeve prior to mounting the sleeve to the body of the surgical instrument, thereby providing a very simple assembling of the elements to provide an assembled surgical instrument ready for use. The pattern light source, the power source, the projector and/or the control unit is/are preferably fixed to the sleeve by being fully or partly integrated in the material of the sleeve, by being arranged between layers of the sleeve by being mechanically attached to the sleeve e.g. by being arranged in a pocket of the sleeve and e.g. fixed there by being attached by being connected to another element (such as another of the parts attached to the sleeve). In an embodiment one or more parts of the pattern light source, the power source, the projector and/or the control unit is/are mechanically attached to the sleeve by an adhesive, by welding, by screws, by rivets or by any other suitable means.

In an embodiment the pattern light source and the battery is incorporated into a pattern light source housing together with the projector to form the pattern generating member and the pattern generating member is fixed (temporally or permanently fixed) to the sleeve prior to mounting the sleeve to the body of the surgical instrument.

In an embodiment, the pattern generating member projects the light pattern on an area in front of the body portion covering 90 degree to the sides, preferably 60 degree. In front of the body portion, is to be understood as along the longitudinal axis of the body portion and away from the handle portion (in distal direction), preferably in front of the surgical tool.

In an embodiment the projector of the pattern generating member is configured such that when it is fixed to the body portion of the surgical instrument it is arranged for emitting a pattern comprising a plurality of projecting directions with angles relative to its longitudinal axis of from about 5 degrees to about 85 degrees (or even up to 90 degrees), such as from about 10 degrees to about 60 degrees, such as from about 15 degrees to about 50 degrees.

When the projector of the pattern generating member is fixed to the body portion of the surgical instrument it is adapted to emitting a pattern such that a movement of the surgical tool results in a correlated change of the pattern.

The pattern may have any desired shape. In case the pattern consists of one or more coaxial circles any non-rotational movements of the surgical tool advantageously results in a correlated change of the pattern.

The change of the pattern may e.g. be a change of shape, position, size and/or color.

In an embodiment the projector is fixed or adapted to be fixed to the body portion of the surgical instrument such that the pattern remain substantially stationary when the surgical instrument is subjected exclusively to circumferential movement with the longitudinal axis of the body portion of the surgical instrument as center of the circumferential movement.

In an embodiment the projector when fixed to the body portion of the surgical instrument, is configured for emitting a pattern which pattern when projected to a surface perpendicular to the distal direction is at most 10 fold rotational symmetrical, preferably the pattern is at most 8 fold rotational symmetrical.

Such pattern which is not fully rotational symmetrical but has up to 10 fold rotational symmetry gives the user an even better visual information about the position of the surgical instrument and in particular the surgical tool. For example the user can with a high precision see any twisting and angular movements of the surgical tool.

In an embodiment, the light pattern is a grid. Thus, the light pattern is a light grid which is projected on an area of the surgical field when the surgical instrument is in use. The changes in the grid lines can for example be used to deduce the contours of the body cavity such as projected surface and/or the contours of the surgical field. The changes in the angle and distance between crossing and/or parallel grid lines when the surgical instrument is moved can for example be used to determine the orientation of the surgical instrument.

The phrases "surgical field", "surgical site" and "surgery target site" are herein used interchangeable. In certain situations, as it will be explained below, the surgical site is an artificial surgical site.

In an embodiment the light pattern comprises a plurality of light dots. When the surgical instrument is moved, the position and/or the distance between the dots will change, which enhances the surgeon's ability even further to deduce the position of the surgical instrument and the area contours of the surgical field.

In an embodiment the projector fixed to the body portion of the surgical instrument is configured for emitting a pattern which pattern, when projected to a surface perpendicular to the longitudinal axis of the body portion of the surgical instrument, comprises a plurality of angled lines. Advantageously the pattern comprises a grid of lines, such as a grid comprising one or more sets of parallel lines.

Where the pattern has angled lines pattern when projected to a surface perpendicular to the distal direction a tilting of the surgical instrument can for example be observed by a change of such angled lines e.g. by a deformation of one or more of the lines, by change of line angles and/or by change of distance between lines.

The pattern is advantageously sufficient large to ensure good visual perception of the surgical tool and movement thereof—even when the surgical tool is in contact with tissue during a surgery.

In an embodiment the projector in mounted condition (i.e. fixed to the body portion of the surgical instrument) is configured for emitting a pattern which pattern, when projected to a projecting surface immediately distal to the surgical tool and perpendicular to the longitudinal axis of the body portion of the surgical instrument, has a pattern beam size determined as the diameter of a circle inscribing the pattern of at least about 0.5 cm, such as up to about 60 cm, preferably from about 1 cm to about 25 cm. Thereby the user can be guided by the pattern and deformations of the pattern even when the surgical tool is close to or even touching the tissue.

Advantageously the pattern projected to a projecting surface becomes larger the larger the distance to the projecting surface. In an embodiment, the pattern beam size increases proportionally on a projecting surface when the surgical instrument is moved to a distance between the surgical tool and the projecting surface. Advantageously the pattern beam size increases such that at a distance of 1 cm the pattern beam size is at least about 5% larger than at zero distance. In an embodiment the pattern beam size increases such that at a distance of 1 cm the pattern beam size is at least about 10% larger, such as up to 200% larger than at zero distance.

The invention also comprises a surgical system suitable for performing minimal invasive surgery or suitable for training for performing minimal invasive surgery.

The surgical system comprises an illuminating element comprising an illuminating light source for illuminating a surgery target site, a camera element for acquiring images of the surgery target site, a monitor for displaying the acquired images and at least one surgical instrument assembly.

The surgical instrument assembly comprises a surgical instrument and a pattern generating member. The surgical instrument has a distal end and a proximal end and comprises a handle portion at its proximal end, a surgical tool at its distal end and a body portion connecting the handle portion to the surgical tool. The pattern generating member comprises a pattern light source and a projector, wherein the pattern light source is operatively connected to the projector for projecting a light pattern. At least the projector of the pattern generating member is at least temporarily fixed to the body portion of the surgical instrument such that a movement of the surgical tool results in a correlated movement of the projector.

In an embodiment at least any non-rotational movement of the surgical tool results in a correlated movement of the projector.

Advantageously the surgical instrument assembly is an assembled correlated set as described above.

The camera element can be any element capable of acquiring images of a surgery target site. In an embodiment the camera element is in form of an endoscope, such as a rigid endoscope or a flexible endoscope. Such rigid and flexible endoscopes are well known in the art and any such prior art endoscopes may form the camera element of the surgical system.

The camera element is operatively connected e.g. wireless or by wire to the monitor optionally via a computer and/or via the Internet. The camera may e.g. comprise an objective lens and a lens system transmitting the image from the objective lens to the monitor, typically a relay lens system in the case of rigid endoscopes or a bundle of fiber optics in the case of a flexible endoscope (fiberscope).

The illumination element can be a separate illumination element or it can e.g. be incorporated in the camera element e.g. in the endoscope.

In an embodiment the surgical system comprises an endoscope comprising both the illumination element and the camera element. Where the endoscope comprises both the illumination element (or the illumination instrument) and the camera element these parts are advantageously integrated into the endoscope. In an embodiment the endoscope may comprise a channel for the illumination element.

The illumination light source is normally outside the body and the illumination light is typically directed via an optical fiber system.

In an embodiment the camera element is an endoscope, comprising a channel for the surgical instrument assembly.

In an embodiment the illumination element comprises an illuminating instrument and an illuminating light source operatively connected to the illumination instrument, the illumination light source is preferably adapted to be positioned at a distance to the illumination instrument and is preferably operatively connected to the illumination instrument via an optical fiber.

The illumination instrument is not operatively connected to the surgical instrument to change position in dependence on the position of the surgical tool of the surgical instrument.

The illumination instrument is the element from where the illumination is emitted. The illumination element may be a projector for the illumination light, such as a projector comprising a phase optic element, a spatial light modulator, a multi-order diffractive lens, a holographic lens, a Fresnel lens and/or a computer regulated optical element as described above.

The illumination light can be any kind of light, e.g. the illumination light as used in prior art illumination elements. The illumination light source may be a coherent or an incoherent light source. In an embodiment illumination light source is a halogen light source, an arc light source and/or a LED light source.

In an embodiment illumination light source is an arc light source such as a xenon source for illumination.

In an embodiment the illumination light source is selected from a VCSEL light source and a supercontinuum light source.

Outstanding illumination light sources are ones that combine high color rendering, high luminance and as little ultraviolet and infrared radiation as possible.

Generally it is desired that the illumination light source has a relatively large band width in order to provide a good illumination. Advantageously the illumination light source has a band width comprising visible light having wavelength in the range from about 400 nm to about 900 nm, preferably in the range from about 450 nm to about 700 nm, preferably in the range from about 500 nm to about 650 nm. As described below the illumination element may comprise a filter e.g. an on-off filter or a tunable filter in case the surgeon wishes to observe certain tissue illuminated with narrow band width light.

Preferably the illumination light source has a band width (full width at half maximum—FWHM) of at least about 50 nm, such as from about 60 nm to about 800 nm or larger.

Preferably the illumination light source and the pattern light source differ from each other such that the surgeon or a computer can distinguish light pattern reflected light from illumination reflected light. Preferably the pattern light source has a narrow bandwidth relative to the bandwidth of the illumination light source. In an embodiment the pattern light source has a bandwidth which is about half or less than the bandwidth of the illumination light source. In an embodiment the pattern light source has a bandwidth which is 1/10 or less than the bandwidth of the illumination light source.

In an embodiment the pattern light source comprises wavelength in its bandwidth which has a higher power than in the bandwidth of the illumination light, thereby the surgeon or the computer can distinguish light pattern reflected light from illumination reflected light.

In an embodiment the pattern light source comprises wavelength in its bandwidth which are not comprised in the bandwidth of the illumination light source. Preferably the pattern light source comprises wavelength below 550 nm, and the illumination light source does not comprises wavelengths below 550 nm.

In an embodiment the illumination light source and or the illumination instrument comprises an optical filter, such as a tunable optical filter and/or an on-off filter. Thereby a user can switch from a broad band illumination emitted to the surgery target site to a narrow band illumination e.g. to observe certain tissue in certain light to reveal defects In an embodiment, data of the wavelength of the reflected light of the light illumination or of the light pattern may be obtained and a system may be adapted to receive the data and determine properties of tissue in the surgical site. By analyzing the reflected light, certain properties of the tissue may be determined. This can for example be the oxygen level in the tissue and changes thereof, and the type of tissue. For example the reflected light can be used to determine what kind of organ the tissue is part of, which indicates to the surgeon what organs are which and thereby assisting the surgeon to the area of interest.

In an embodiment the surgical system further comprises a marking element comprising a marking instrument and a marking light source. The marking element is applied for marking up the surgery target site e.g. with a marking light pattern e.g. a dotted pattern or a grid. Such marking pattern is independent of the position of the surgical tool and the pattern does not change in a correlated way relative to movement of the surgical instrument or the surgical tool of the surgical instrument. Preferably the marking pattern is kept substantially stationary (or simply switched on and of) during a surgery. The marking instrument is e.g. a projector for the marking light and is e.g. arranged on the endoscope.

The marking light source advantageously differs from the pattern light source and the illumination light source, preferably the marking light source has a band width (full width at half maximum—FWHM) of up to about 50 nm, such as from 1 nm to about 20 nm.

In an embodiment the marking light source is as the invisible light source described in WO 2013/163391.

In an embodiment the marking the marking light source comprises visible light.

In an embodiment the marking element is as the projector assembly of the metrology system described in US 2013/0296712.

The invention also comprises a training kit suitable for training for performing a minimal invasive surgery.

The training kit comprises a surgical system as described above, an artificial surgical site and a cover for the artificial surgical site, wherein the cover comprises one or more through holes for the surgical instrument assembly. The cover may e.g. be shaped as a screen, a plate, a curtain, a curved shield or any combinations thereof.

The camera element is configured for acquiring images of the artificial surgical site and may e.g. be as described above. In an embodiment the camera element is fixed to the cover on a side of the cover facing the artificial surgical site. In an embodiment the camera element is arranged to be inserted through the one or more through holes.

The illumination element is configured for emitting light towards the artificial surgical site and may e.g. be as described above. In an embodiment the illumination element is fixed to the cover on a side of the cover facing the artificial surgical site. In an embodiment the illumination element is arranged to be inserted through the one or more through holes.

Advantageously the illumination element and the camera element optionally in form of a combined illumination element/camera element is/are fixed to the cover. In an embodiment the illumination element and the camera element optionally in form of a combined illumination element/camera element have/has a proximal end and a distal end wherein the camera element and illumination element carries a camera lens and an illuminating emitter at their/its distal end and wherein the one or more through holes are adapted, such that the distal ends of the surgical instrument and the camera element/illumination element can be inserted through the one or more holes.

Advantageously the camera element is in data connection (wireless or by wire) with a computer programmed to monitoring the movement of the surgical tool of the surgical instrument. Preferably the computer is programmed to monitoring the shape and size of the light pattern as a function of time and based thereon determine the movements of the surgical tool. Advantageously the computer further is programmed to evaluate the performance of the user.

The term "computer" is used to mean any kind of computer or systems of computers. The computer may e.g. be a single computer or two or more computers in data connection.

Where the surgical system also comprises a marking element e.g. emitting narrow band UV or IR this generated marking pattern may e.g. provide a reference grid for the computer to determine the positions and movements of the surgical tool.

The invention also comprises a method of training for performing a minimal invasive surgery comprising training handling of a surgical instrument for minimal invasive surgery.

The training method comprises
  providing a surgical instrument assembly, wherein the surgical instrument assembly comprises a surgical instrument and a pattern generating member, the surgical instrument has a distal end and a proximal end and comprises a handle portion at its proximal end, a surgical tool at its distal end and a body portion connecting the handle portion to the surgical tool, the pattern generating member comprises a pattern light source and a projector, wherein the pattern light source is operatively connected to the projector for projecting a light pattern, at least the projector of the pattern generating member is at least temporarily fixed to the body portion of the surgical instrument such that a movement of the surgical tool results in a correlated movement of the projector, and
  performing a plurality of training steps, each step comprises arranging the surgical instrument with its distal end pointing towards a training surface such as a surgery target site or an artificial surgical site, emitting a light pattern from the projector, such that a light pattern is reflected from the training surface, moving the surgical instrument and observing the corresponding changes of the light pattern.

In an embodiment, the projected light pattern is adapted to be able to change shape, position, size and/or color. The surgeon can then ensure that the light pattern has the optimal form and/or extension and/or position on the surgical area for further enhancing the surgeon's ability to coordinate movement of the surgical instrument based on the indirect vision. In an example the color of the light pattern is chosen such that specific objects in the surgical field appear clearer and/or with a larger contrast in relation to other objects in the surgical filed. This can be used to highlight an object in the surgical field, for example an organ which is the target for the surgical procedure.

In an embodiment the training method comprises the steps: provide a cavity, provide a system for indirect vision of an area of the cavity, insert the surgical tool of the surgical instrument assembly and at least a section of the body portion into the cavity, project the light pattern on a wall of the cavity visible by the system for indirect vision, move the instrument and observe, via the system for indirect vision, the correlated changes of the light pattern.

In an embodiment, data on shape, position, size and/or color and/or changes thereof of the light pattern is obtained and a computer is programmed to receive the data and determine the position of the surgical tool. The position of the tool is advantageously forwarded to the surgeon. The position of the surgical tool can for example comprise information of the distance between the surgical tool and a training surface, such as a surgical target site or an artificial surgical site. This distance can be presented on a monitor used for remote vision e.g. as a distance in mm. The distance can be given for any distance between the surgical tool and another object in the body cavity.

Thus, it is possible to train the handling of a surgical instrument assembly based on remote vision of a section of the surgical instrument inside a cavity. Using this method for training, the handling of the surgical instrument assembly, will enhance the ability to transform the information obtained by indirect vision into a spatial understanding of the position of the instrument and internal contours of the cavity. Hence, it will train the ability to correctly connect the visual perception and motor system (hand-eye coordination) when observing via remote vision.

In an embodiment, the method is adapted such that data of the position of the surgical tool and/or changes of the light pattern is obtained and forwarded to a computer, and wherein the computer is adapted to determine the abilities of an operator of the surgical instruments based on an evaluation of the data of the position and/or changes in the light pattern.

Advantageously the surgeon in training will move the surgical instrument assembly during training in order to perform the task given. If the shape, position, size and/or color and/or changes thereof of the light pattern is recorded by the computer connected to the remote vision, (e.g. via a laparoscope) the surgeon's ability to handle the surgical instrument assembly can be determined. For example, if the light pattern has repetitive changes it can indicate that the operator makes the same movements of the surgical instruments several times and thus have difficulty doing a specific task, for example aligning the instrument for grapping a specific item in the artificial surgical site. Thus, the computer can so to speak, give a mark of the performance of the surgeon in a training session based on data of the shape, position, size and/or color and/or changes thereof of the light pattern. It is to be understood that the abovementioned feature also can be used during live surgery for evaluating the surgeon's capabilities during the surgical procedure.

In an embodiment the training method comprises at least one training step of moving the surgical tool to and back and forth relative to the training surface and observing the corresponding changes of the light pattern.

In an embodiment the training method comprises at least one training step of moving the surgical tool by twisting and/or tilting relative to the training surface and observing the corresponding changes of the light pattern.

Advantageously the surgical instrument assembly is part of a surgical system as described above and/or the surgical instrument assembly is part of a training kit as described above. In an embodiment the training method comprises inserting the distal ends of the camera element and illumination element through the one or more holes of the cover towards the artificial surgical site, illuminating the artificial surgical site by the illumination element, acquiring images of the artificial surgical site by the camera element and transmitting the acquired images to the monitor for displaying the acquired images, inserting the surgical tool of the surgical instrument through a hole of the cover and emitting a light pattern towards the artificial surgical site, moving the surgical instrument relative to the training surface, such as a surgery target site or an artificial surgical site and observing the light pattern imaged on the monitor and changes thereof corresponding to the respective movements of the surgical instrument.

In an embodiment the method further comprises evaluating the performance of the training person by monitoring the shape, position, size and/or color and/or changes thereof of the light pattern as a function of time and based thereon determine a sequence of movements of the surgical tool and evaluate the performance. The performance advantageously is evaluated by benchmarking the movements of the surgical instrument to a preset sequence of movements.

The invention also comprises a method of performing a minimal invasive surgery of a target surgical site in an internal body structure below a skin area of a patient. The surgery method comprises providing access to the surgical target site comprising providing an incision through the skin area, inserting an illumination element for illuminating a surgery target site, a camera element for acquiring images of the surgery target site, and at least one surgical instrument assembly through the incision. The camera element is operatively coupled to a monitor for displaying the acquired images. The laparoscopic instrument assembly comprises a surgical instrument with a surgical tool and a pattern generating member with a pattern light source and a projector for projecting a light pattern, which projector is correlated to the surgical tool such that movements of surgical tool results in a change of the pattern of the pattern light source, and wherein the method comprising handling the surgical instrument based at least partly on visualizing of the light pattern by the acquired images on the monitor.

Advantageously the surgical instrument assembly is part of a surgical system as described above and/or the surgical instrument assembly is part of a training kit as described above.

All features of the inventions including ranges and preferred ranges can be combined in various ways within the scope of the invention, unless there are specific reasons not to combine such features.

BRIEF DESCRIPTION OF DRAWINGS

The invention will be explained more fully below in connection with a preferred embodiment and with reference to the drawings in which:

The figures are schematic and are not drawn to scale. FIG. 1 discloses a surgical instrument assembly 1, in the present case a laparoscopic instrument. The surgical instrument assembly 1 comprises a surgical instrument with a handle portion 2 and a body portion 3 with a surgical tool 4 in the present case forceps. The body portion interconnect the handle portion 2 which is arranged at the proximal end of the surgical instrument and the surgical tool 4, which is arranged at the distal end of the surgical instrument. The body portion is arranged in the distal/proximal direction.

Figure 1:
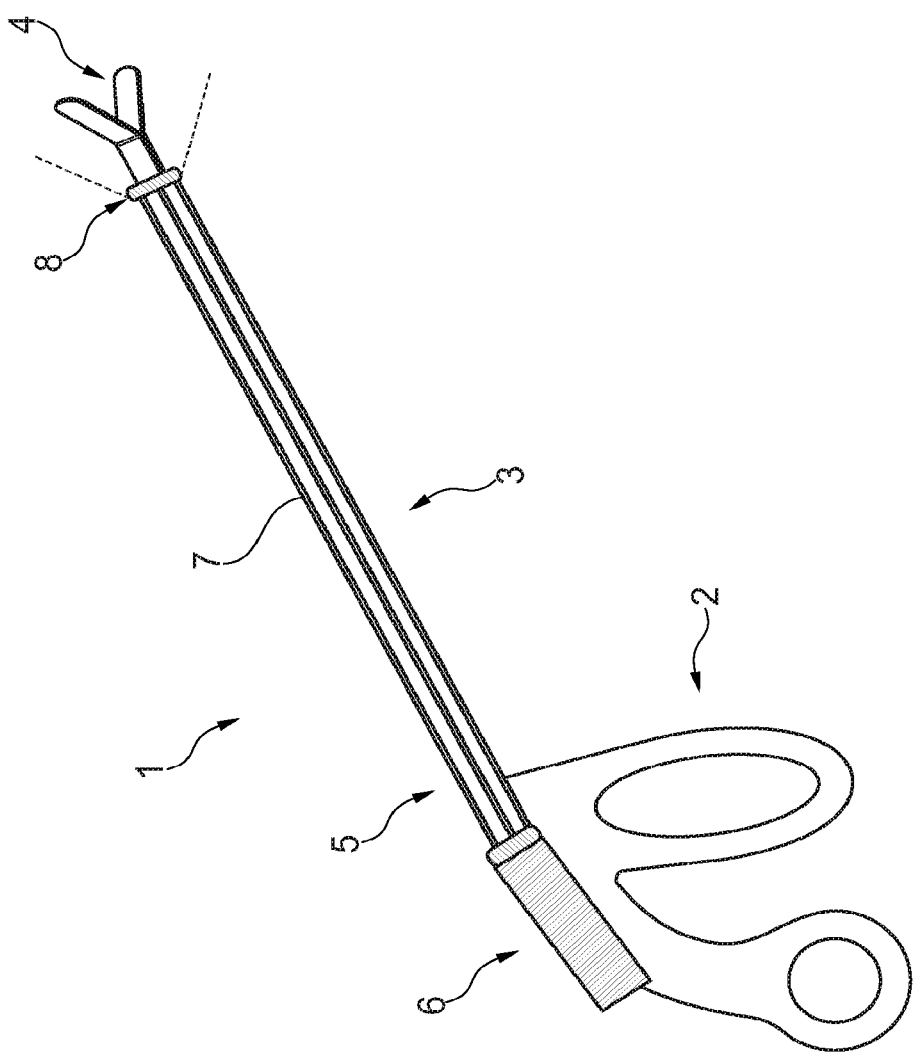
FIG. 1 is a schematic view of an embodiment of a surgical instrument assembly comprising an assembled set of a surgical instrument and a pattern generating member.

In another embodiment the surgical tool 4 can be another surgical tool e.g. scissors or as described above. The surgeon holds the handle portion 2 and can in this way control the surgical instrument assembly and by pressing or manipulating the handle portion the forceps can be controlled.

The surgical instrument assembly 1 further comprises a pattern generating member 5 comprising a pattern light source 6 and optical fibers 7 which guide the light to a projector 8 (light emitting portion) where optical fibers 7 ends and the light is projected from the projector 8 in a desired pattern. The pattern light source 6 is placed on or incorporated into the handle portion 2 of the surgical instrument and is thus not inserted into the body cavity during surgery. In an embodiment the pattern light source 6 is connected to a battery which is also placed or incorporated into the handle portion 2. In an embodiment the pattern light source 6 is connected to an external power source such as a battery which is an external battery arranged at a distance from the surgical instrument assembly.

The projector 8 has advantageously a spherically periphery geometry and is configured for emitting a light pattern comprising a plurality of angled lines and or a plurality of parallel lines. In an embodiment the projector 8 has for example a spherical geometry, and is shaped for emitting a light pattern with a spherically periphery where the light pattern forms a light pattern resembling the light pattern generated by a mirror ball. It is to be understood that the mirror ball resembling pattern is preferably only a section of normal mirror ball pattern, e.g. not a 360 degree pattern but preferably only a 90 degree section of the pattern and/or with an angle relative to the axis of the body portion 3 up to 85 degrees.

This light pattern makes it possible for the user of the surgical instrument assembly 1 to deduce the position and movements of the surgical instrument assembly 1 and thus the surgical tool 4, relative to the surface e.g. a surgical site where the light pattern is projected.

The light generated in the light source 6 may be generated by use of one or more LED's and/or lasers or a combination thereof as explained above.

A section—i.e. the distal end of the body portion 3 of the surgical instrument assembly 1 shown in FIG. 1 is adapted to be inserted into a body cavity of a patient through small incisions. The surgeon then seizes the handle portion 2 with his or hers hands in order to perform the surgical procedure. A not shown endoscope, e.g. a laparoscope, may also be inserted into body cavity in order to let the surgeon see the surgical field where the surgical procedure is to be performed. The endoscope can comprise an illuminating instrument and a camera element e.g. a video camera such that the surgeon can see the surgical field and the surgical tool 4 during the procedure via a monitor. The projector 8 of the pattern generating member 5 is inserted into the body cavity together with the surgical tool 4. The projector 8 will then project a light pattern onto the surgical field. The light pattern will aid the surgeon to interpret the position and the contours of the surgical field. The light pattern aids the surgeon to connect his visual perception of the surgical area which is based on observing the monitor (two-dimensions) with his or hers motor system which is used to control the surgical tools which are moved within the body cavity (in three-dimensions).

The pattern generating member 5 or parts thereof can be made as an optionally removable clip-on device and/or it can permanently attached to the body portion 3. In an embodiment the entire pattern generating element 5 is mounted to body portion 3 and is adapted for being inserted into the body cavity.

Figure 2:
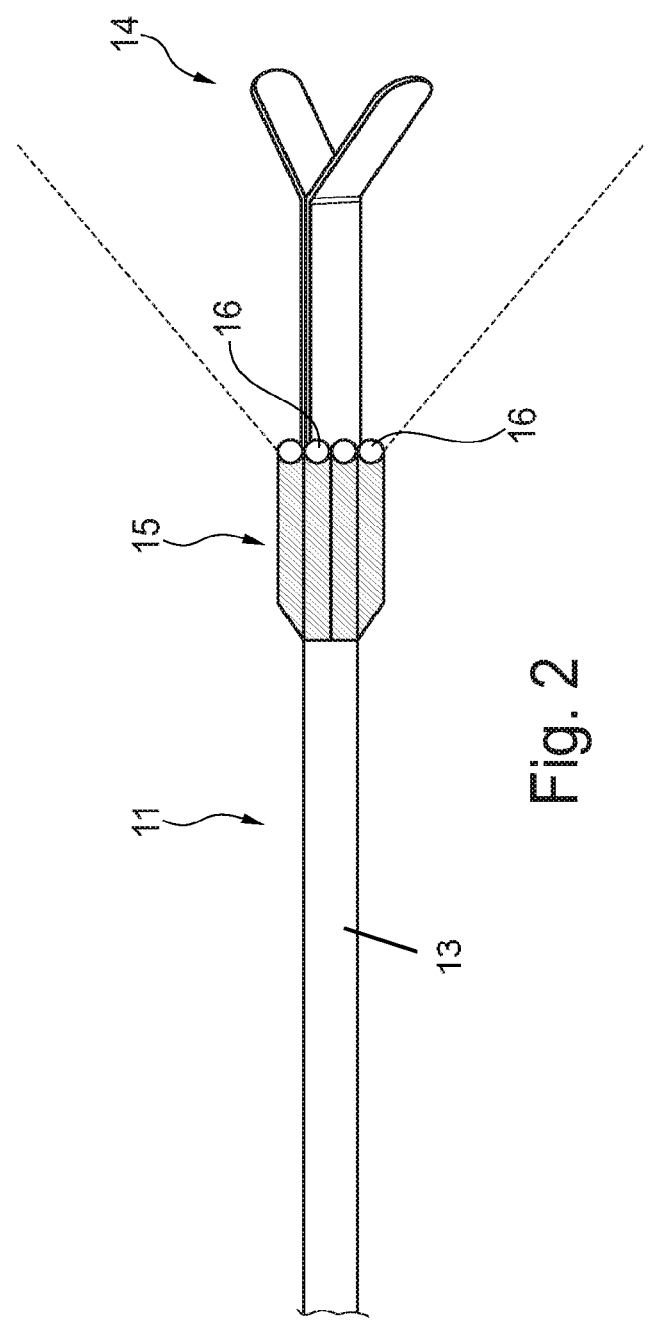
FIG. 2 is a schematic view of a body portion of an embodiment of a surgical instrument assembly comprising an assembled set of a surgical instrument and a pattern generating member.

FIG. 2 shows a body portion 13 of a surgical instrument assembly 11. The body portion 13 has a surgical tool 14 in the form of forceps which can be operated from a not shown handle of the surgical instrument assembly 11. On the body portion 13 there can be seen a pattern generating member 15 with one or more projectors 16 which emits light in an angle in front of the surgical instrument 11, the angle is shown with a dotted line. The pattern generating member 15 has in this embodiment plurality of projectors 16 which emits rays of light that generates a dotted light pattern. The projectors 16 may be optically connected to one or more pattern light sources of the pattern generating member 15. By arranging the projector or projectors with a desired angle the correlation between the movements of the surgical instrument and the change of the projected pattern can be regulated.

Figure 3:
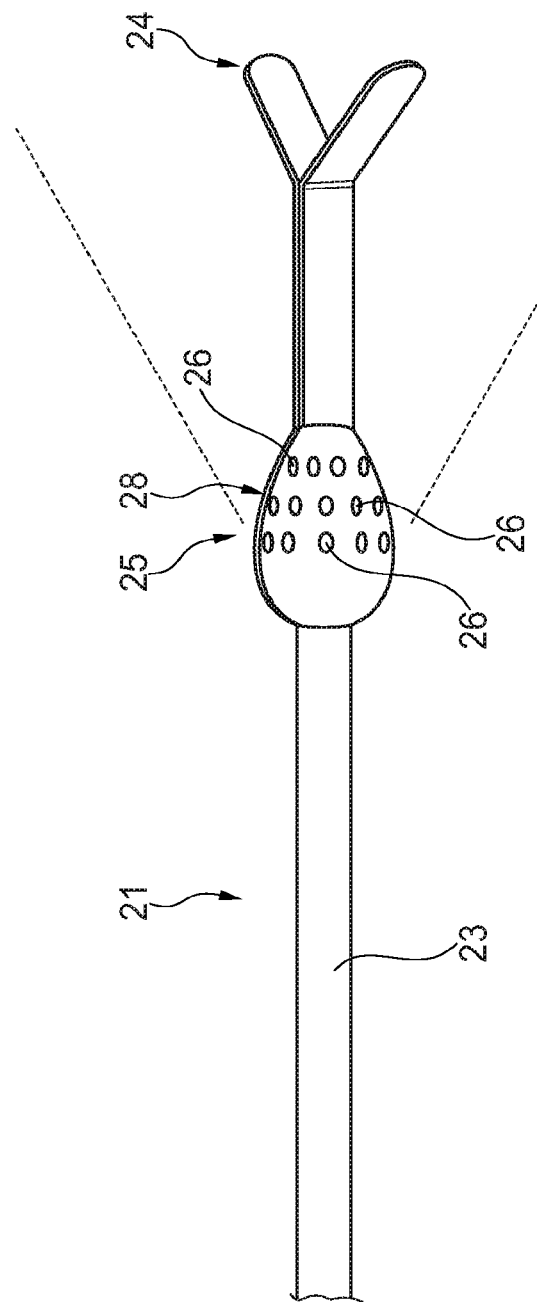
FIG. 3 is a schematic view of a body portion of an embodiment of a surgical instrument assembly comprising an assembled set of a surgical instrument and a pattern generating member.

FIG. 3 shows an alternative embodiment of a pattern generating member 25 mounted onto a body portion 23 of a surgical instrument 21. The pattern generating member 25 comprises a projector 28 with a cylindrical geometry and a plurality of light emitting areas 26 which emits light rays which forms the light pattern. The light emitting areas 26 are arranged in rows and are evenly distributed on the projector 28. The emitting areas 26 of the projector 28 may emit light from the same or from different not shown pattern light sources. The light rays from the light emitting areas 26 is angled such relative to the axis of the body portion 23 that the light ray's closest to the surgical tool 24 is projected to have a smaller angle than the light rays further away from the surgical tool 24. In this way the light pattern can cover a desired large area.

The light source may be constructed so that substantially no light is projected in the direction of the laparoscope in order to prevent light hitting it and thus disturb the view. This can for example be done by turning off or blocking the light which faces the endoscope. It can also be done by constructing the surgical instrument so that there are no lights facing the laparoscope.

Figure 4:
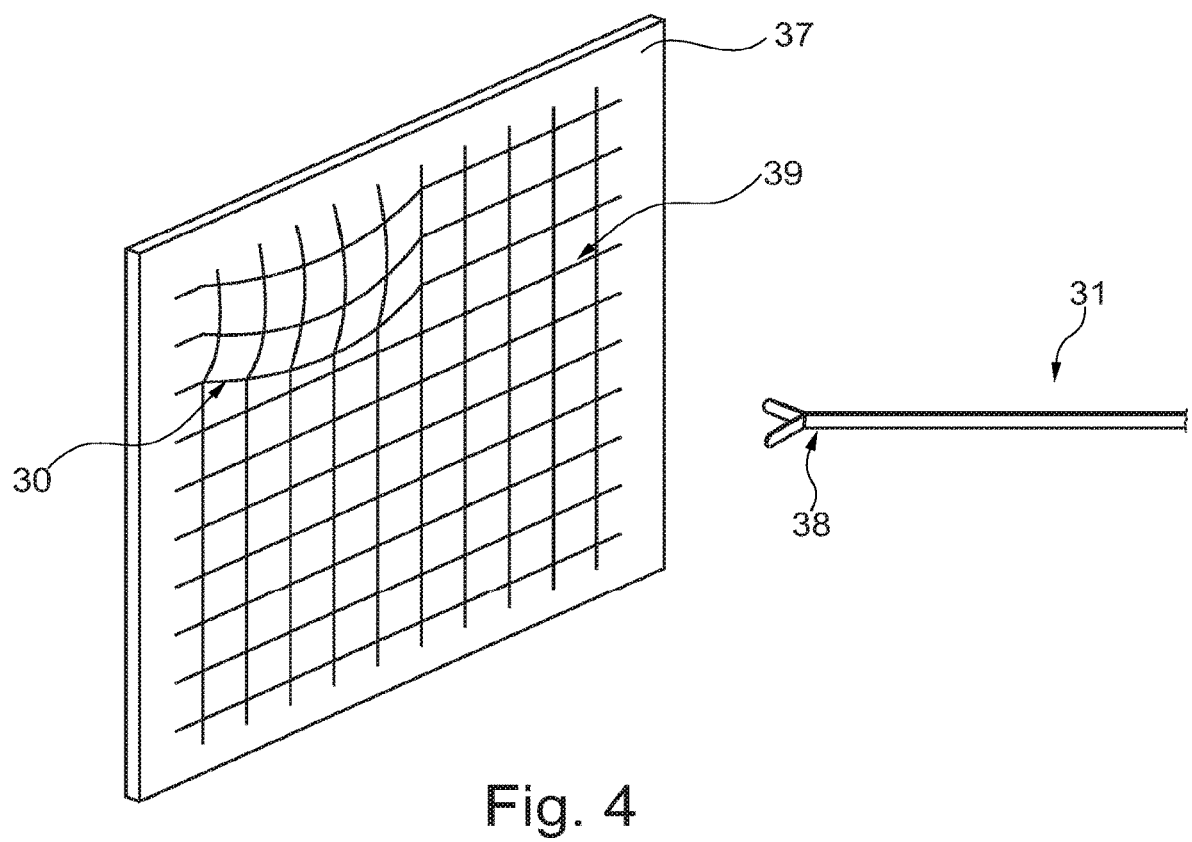
FIG. 4 is a schematic view of a light pattern generated by an embodiment of a surgical instrument assembly comprising an assembled set of a surgical instrument and a pattern generating member.

FIG. 4 is an illustration of a light pattern 39 generated by an embodiment of a surgical instrument assembly 31 assembled from a correlated set of a surgical instrument and a pattern generating element according to the invention, the surgical instrument assembly 31 is shown schematic. The light pattern 39 forms a grid which for illustrative purposes is shown as projected on a board 37 with a bulge 30 in the upper left corner. It can be seen that the grid makes the bulge highly visible as the contours of it stands out. Thus, a surgical instrument 31 with a pattern generating member 38 which projects a light pattern on a surgical field can be used to enhance the visual perception of the three dimensional contours of the surgical field. The operator can in other words deduce the three dimensional contours of the surgical field based on a two dimensional vision of the surgical field.

Figure 5:
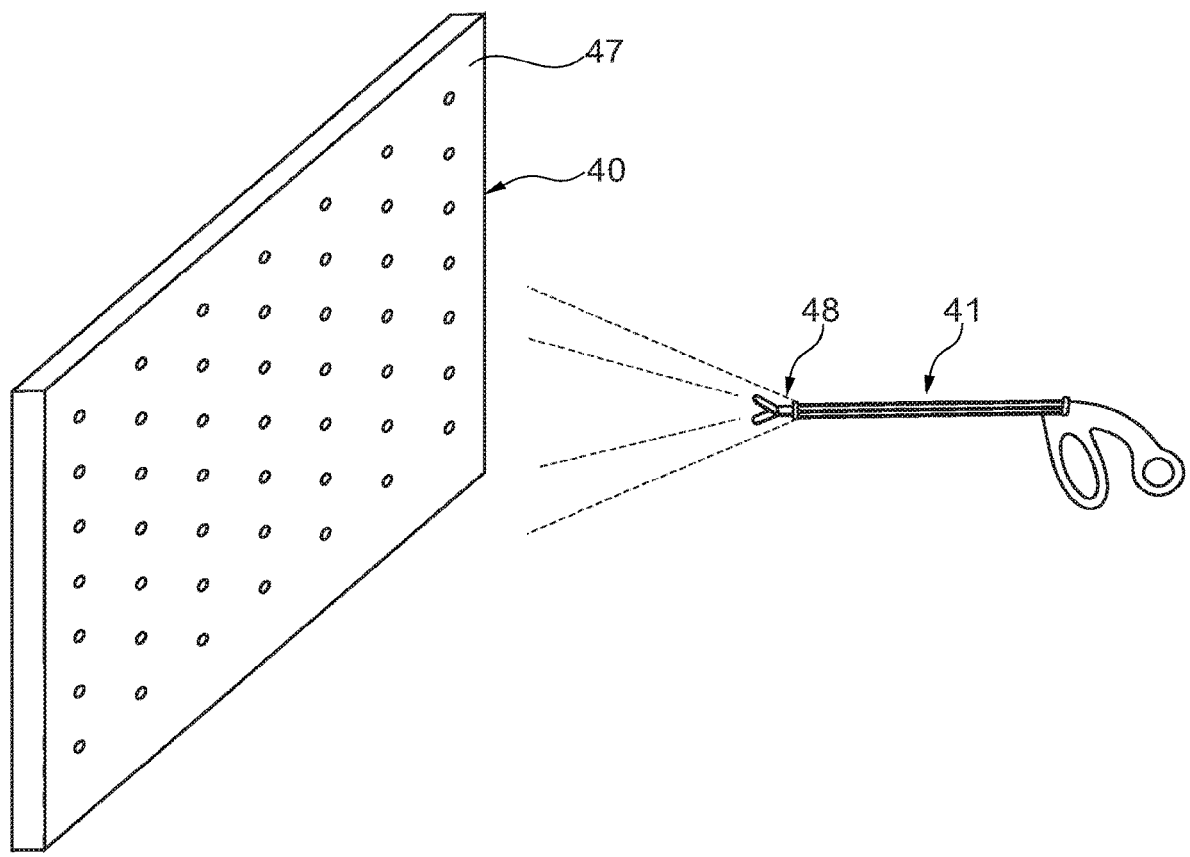
FIG. 5 is a schematic view of a light pattern generated by an embodiment of a surgical instrument assembly comprising an assembled set of a surgical instrument and a pattern generating member.

FIG. 5 shows a schematic view of a light pattern 40 on a board 47, the pattern 40 is generated by a surgical instrument assembly 41. The light pattern 40 comprises a plurality of dots which are projected from the projector 48 on the surgical instrument assembly 41. In similar way as for the light pattern shown in FIG. 4 it is possible for the operator to interpret variations in the light pattern as variation in the surface whereon it is projected and/or to interpret movements of the surgical instrument assembly 41 as correlating changes of the pattern 40.

The light pattern 40 (or 30 as exemplified in FIG. 4) will change shape depending on the position of the surgical instrument. For example, in FIG. 4 the lines of the pattern 30 will become non parallel if the surgical instrument assembly 31 is turned. In addition, the distance between the lines will get smaller if the surgical instrument is moved closer to the board 37 and get larger if the surgical instrument is moved away from the board 37. Thus, it is possible for the operator to deduce the position and orientation of the surgical tool in relation a surface e.g. a surgical site whereon a light pattern is projected based on the geometry light pattern.

Figure 6:
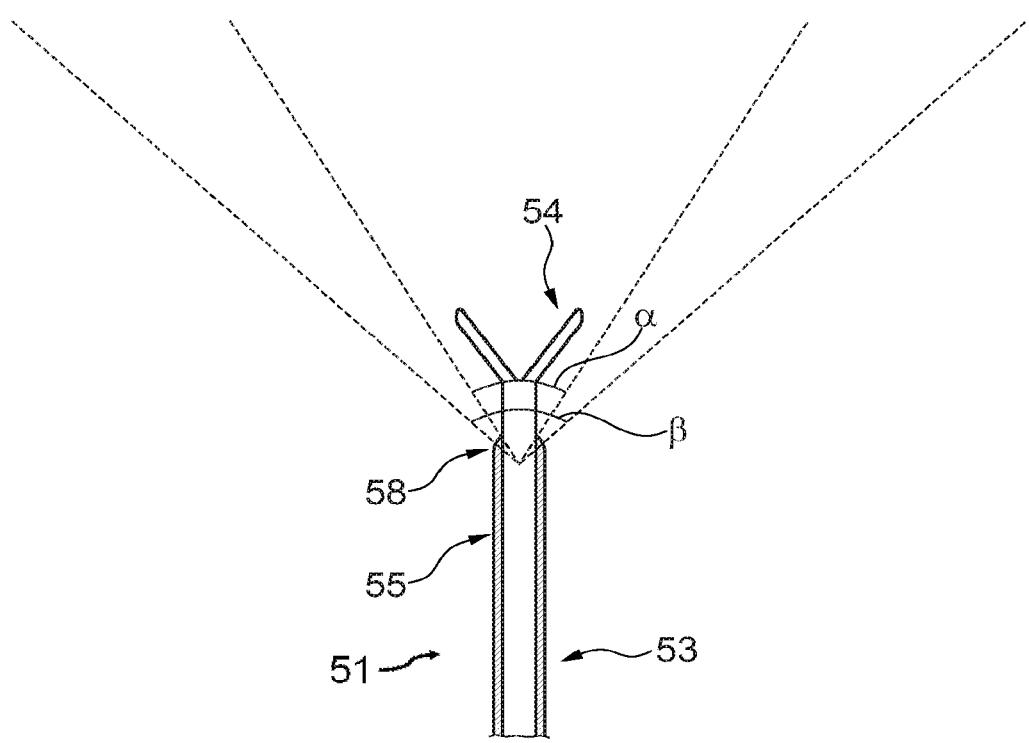
FIG. 6 is a schematic view of a projected light pattern by an embodiment of a surgical instrument assembly.

FIG. 6 shows a body portion 53 of an embodiment of a surgical instrument assembly 51, with a surgical tool 54 and a pattern generating member 55. The figure illustrate that the pattern generating member 55, in one embodiment has a projector 58 which can project the light pattern in an angle between 30° and 65° relative to the axis of the body portion 53. The angle α is 30° and the angle β is 65° relative to the axis of the body portion 53. The light pattern is projected in front of the surgical instrument and can be of a cylindrical geometry such that the projected light pattern will cover a substantially circular area right in front of the instrument when the instrument is held with its distal direction perpendicular to a surface where the pattern is projected onto. It is to be understood that the angles for the light pattern can be any angle and will depend on the specific use of the surgical instrument.

Figure 7:
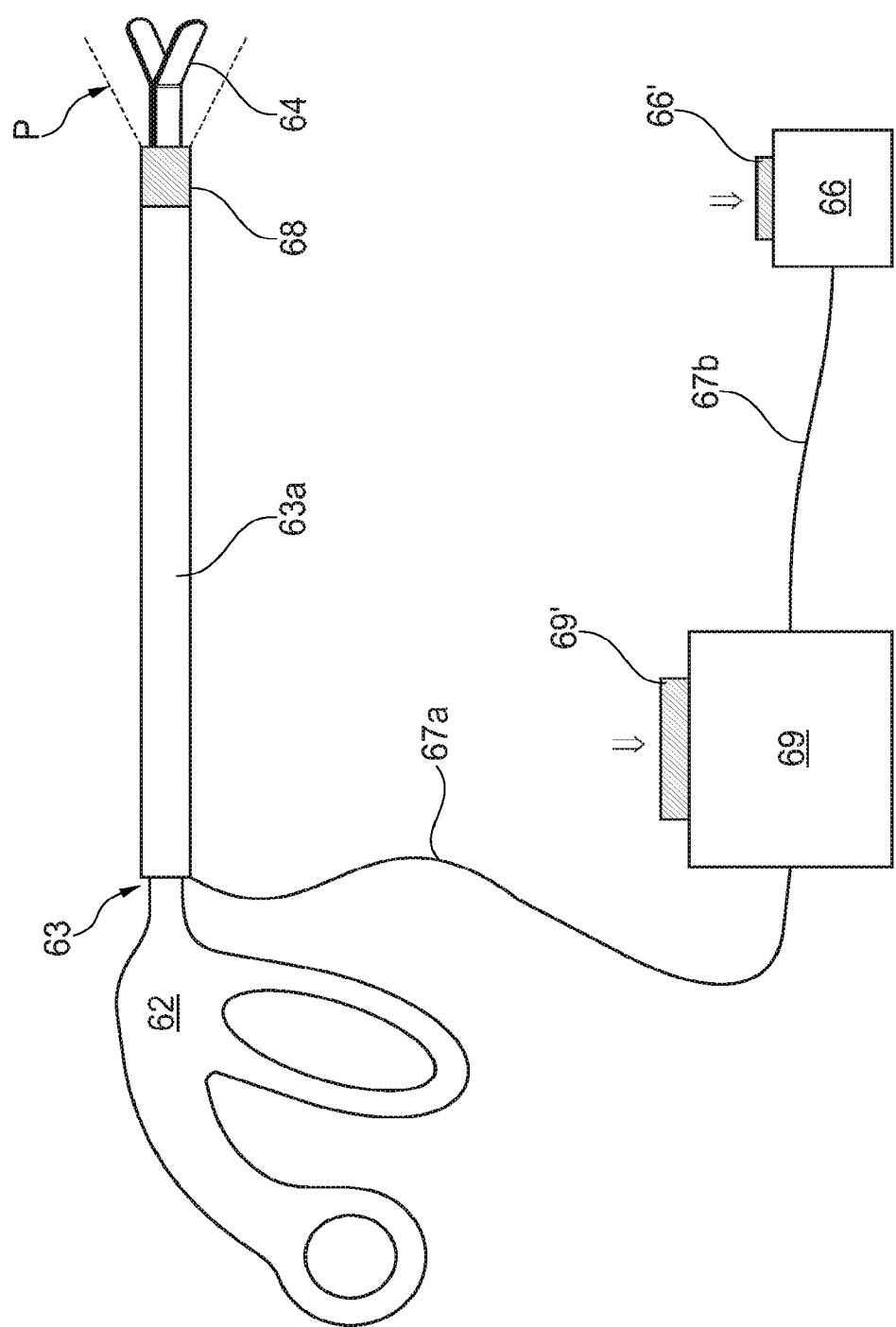
FIG. 7 illustrates a correlated set of an embodiment of the invention comprising a surgical instrument and a pattern generating member where the pattern generation member arranged at a distance from the projector.

The surgical instrument assembly shown in FIG. 7 comprises a correlated set comprising a surgical instrument and a pattern generating member. The surgical instrument comprises a handle portion 62 at its proximal end, a surgical tool 64 at its distal end and a body portion 63 connecting the handle portion 62 to the surgical tool 64. The pattern generating member comprises a pattern light source 66 and a projector 68. The pattern light source 66 is operatively connected to the projector 68 via a pattern light source control unit 69. The pattern light source 66 comprises one or more buttons 66' e.g. for adjusting the pattern light source 66. In the shown embodiment the pattern light source control unit 69 is arranged at a distance from the surgical instrument—e. g. on the floor in form of a pedal with a control button 69', which can be operated by the surgeon. The pattern light source 66 is connected to the pattern light source control unit 69 via an optical fiber 67b and the pattern light source control unit 69 is connected to the projector 68 via an optical fiber 67a. The projector 68 of is at least temporarily fixed to the body portion 63 of the surgical instrument such that a movement of said surgical tool 64 results in a correlated movement of the projector 68. The projector 68 is emitting a light pattern P as described above. The projector 68 is fixed to the body portion 63 of the surgical instrument by a sleeve 63a which surrounds the body portion 63 of the surgical instrument. The sleeve simultaneously holds and protects the optical fiber 67a.

In an alternative embodiment the pattern light source control unit 69 is mounted to or integrated with the handle 62.

Figure 8:
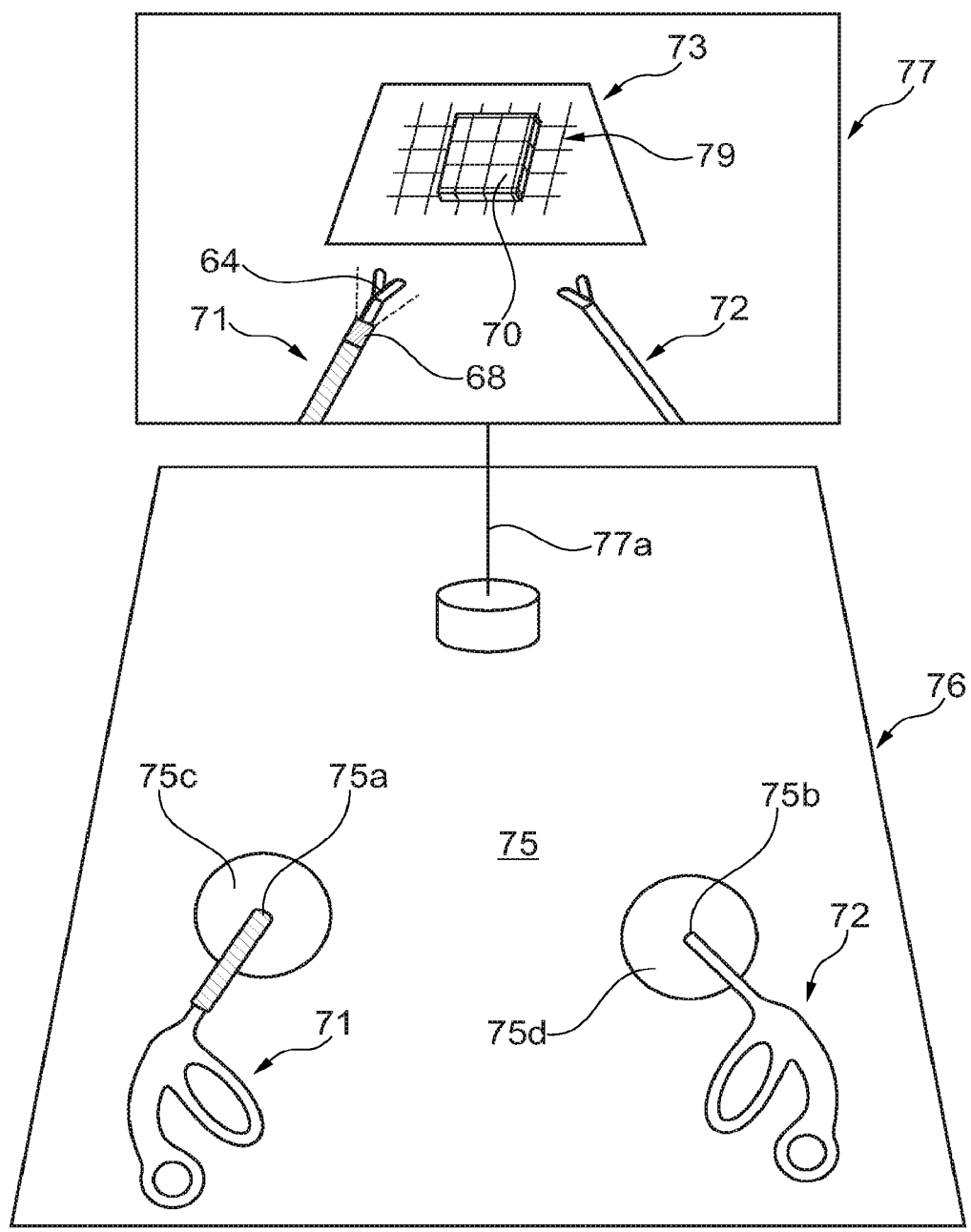
FIG. 8 illustrates a training kit of an embodiment of the invention comprising a surgical system, an artificial surgical site and a cover for the artificial surgical site.

The training kit shown in FIG. 8 comprises a surgical system, an artificial surgical site 73 and a cover 76 for the artificial surgical site. The cover 76 comprises a rear side 75 and an opposite not shown front side facing the artificial surgical site 73. The surgical system comprises a not shown illuminating element placed on the front side of the cover 76 for illuminating the artificial surgical site and a not shown camera element also arranged on the front side of the cover 76 for acquiring images of the artificial surgical site 73. The surgical system further comprises a monitor 77 for displaying the acquired images and at least one surgical instrument assembly 71 e.g. as shown in FIG. 7. The monitor 77 is connected to the camera element via the wire 77a. The cover 76 comprises a through hole 75a for the surgical instrument assembly 71. The through hole 75a comprises a periphery edge 75c of elastic material to provide an elastic seal to the surgical instrument assembly 71. The cover 76 comprises an additional through hole 75b for a further surgical instrument 72 of the surgical system. The through hole 75b also comprises a periphery edge 75d of elastic material to provide an elastic seal to the surgical instrument assembly 72.

The illuminating element is illuminating the artificial surgical site with a broad bandwidth light. The surgical system further comprises a not shown marking element which e.g. in integrated with the illuminating element. The marking element generates a marking pattern 79 which is stationary and used for marking up the surgical site and is e.g. used as a reference pattern. The marking pattern preferably is a narrow band width light pattern e.g. invisible to the human eye. Advantageously the marking pattern can be switched on and off by the surgeon.

The projector 68 generates a pattern 70 which changes when the surgical instrument assembly 71 as described above.

Advantageously the camera element is connected to a computer e.g. integrated with the monitor 77, which computer is programmed to monitoring the movement of the surgical tool 64 of the surgical instrument assembly 71.

Figure 9:
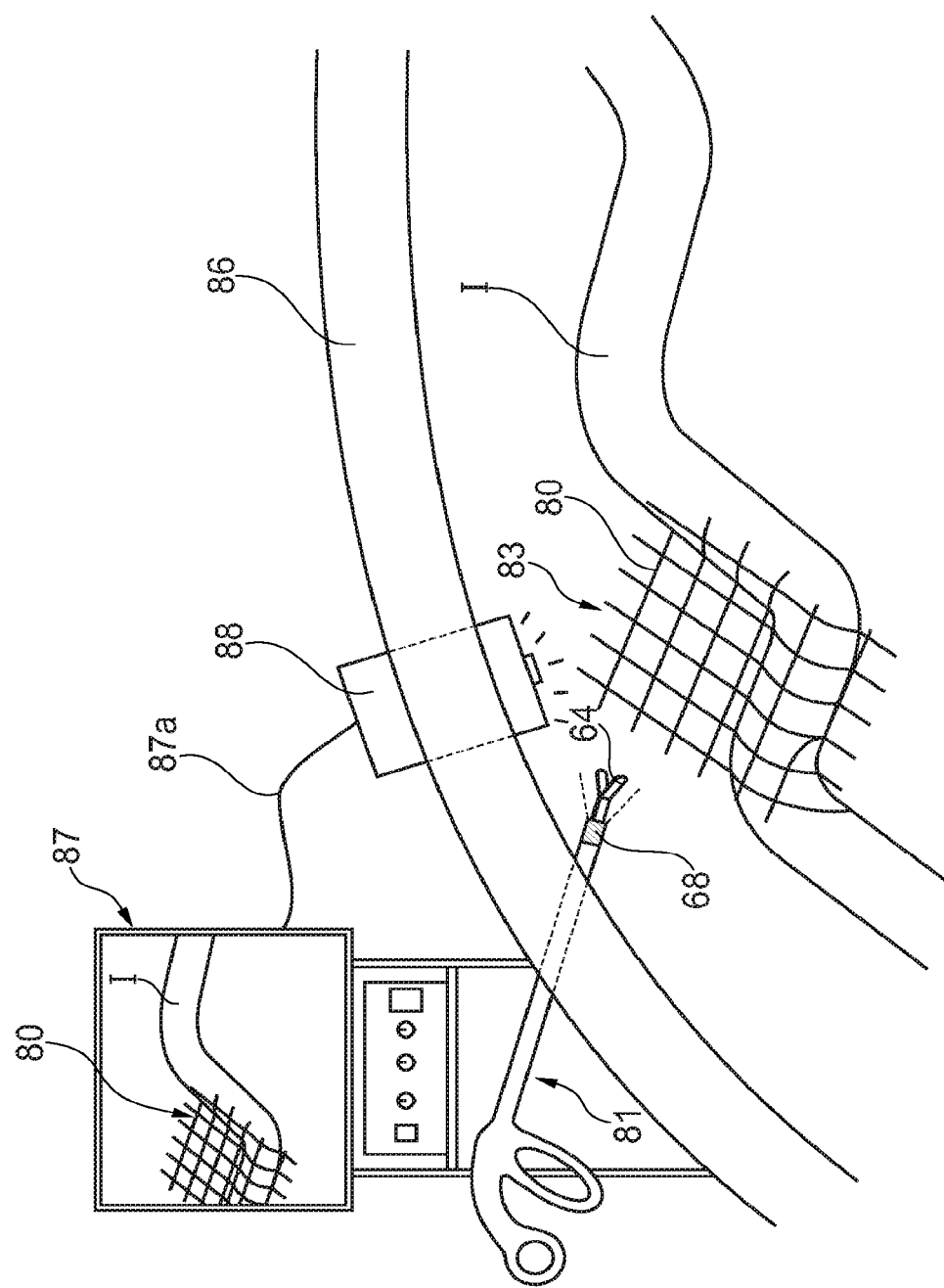
FIG. 9 illustrates a surgical system in use during a minimal invasive surgery.

The surgical system shown in FIG. 9 comprises an illuminating element and a camera element integrated in an endoscope 88. The endoscope may additional comprise a marking element. The endoscope 88 comprises an illuminating light source for illuminating a surgery target sit 83. The illumination light source may e.g. be incorporated into the endoscope or it may be arranged external to the endoscope 88. The camera element of the endoscope 88 is arranged for acquiring images of the surgery target site 83.

The surgical system further comprises a monitor 87 connected to the endoscope with wire 87a. Alternatively the connection between the monitor 87 and the endoscope in wireless connected. The monitor 87 is arranged for displaying the images acquired by the endoscope 88. The monitor may additionally comprise a computer for analyzing the images. The surgical system further comprises a surgical instrument assembly 81 e.g. as shown in FIG. 7. The endoscope 88 and the surgical instrument assembly 81 are arranged with their respective distal ends inserted through an incision in the skin 86 of a patient. Below the skin 86 of the patient is formed an internal body structure leading to the surgery target site 83 e.g. comprising an intestine I. The surgical instrument assembly 81 is arranged such that the projector 68 generates a light pattern 80 onto the surgery target site 83, thereby a movement of the surgical tool 64 results in a correlated movement of the projector 68 and thereby the pattern will change in a correlated way. The surgeon can follow the changes of the pattern 80 on the monitor 87 and thereby he obtains a very good visual spatial perception for handling the surgical instrument assembly 81 during the minimal invasive surgery.

Figure 10:
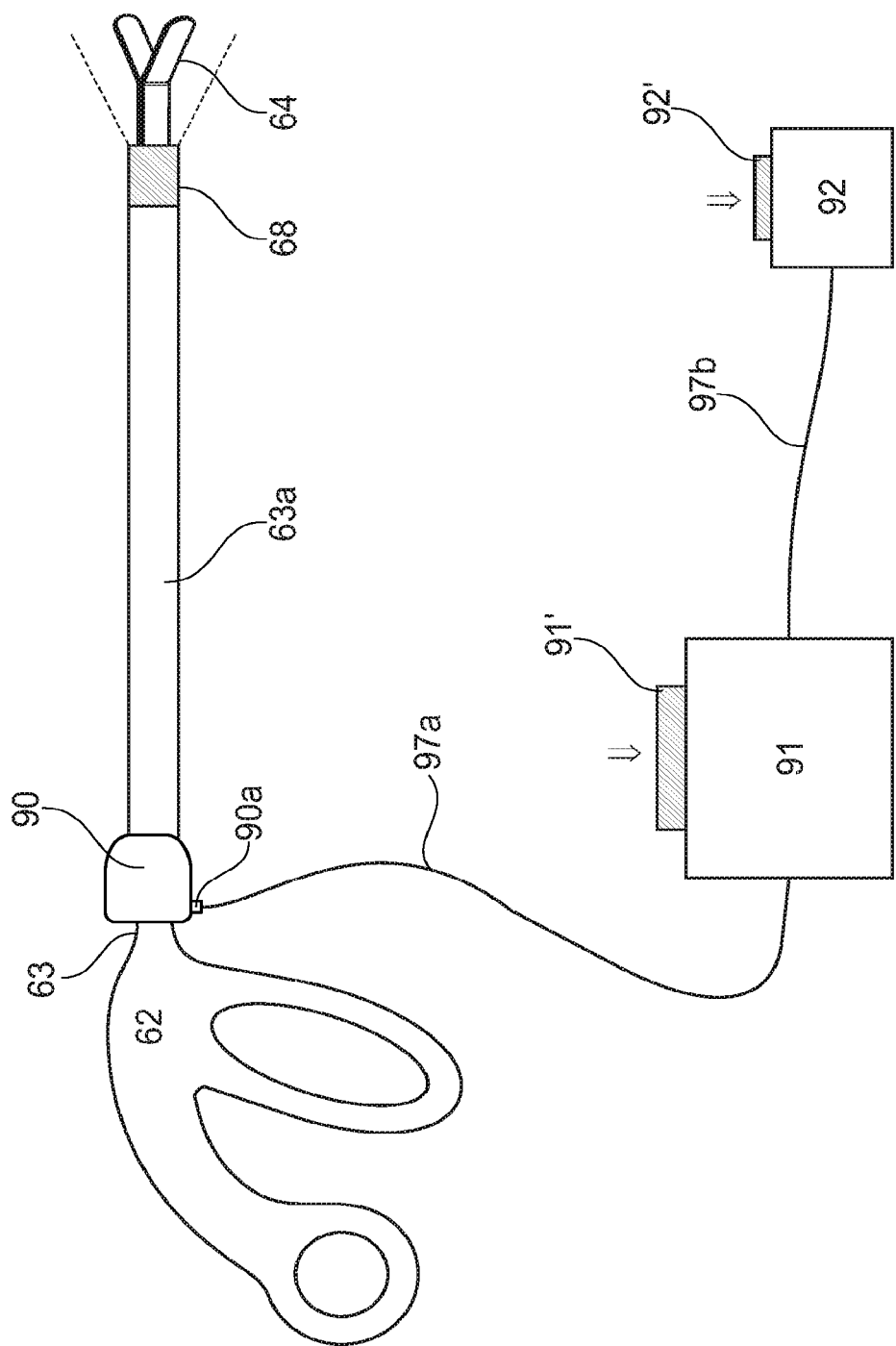
FIG. 10 illustrates another correlated set of an embodiment of the invention comprising a surgical instrument and a pattern generating member.

The surgical instrument assembly shown in FIG. 10 is a variation of the surgical instrument assembly of FIG. 7 and it comprises a correlated set comprising a surgical instrument and a pattern generating member. The surgical instrument comprises a handle portion 62 at its proximal end, a surgical tool 64 at its distal end and a body portion 63 connecting the handle portion 62 to the surgical tool 64. The pattern generating member comprises a pattern light source incorporated into a housing 90. The housing 90 is mounted onto the body 63, either directly or by being attached to the sleeve 63a which surrounds the body portion 63 of the surgical instrument. The projector 68 is fixed to the body portion 63 of the surgical instrument by the sleeve 63a. The projector 68 is for example attached to the sleeve as described above. The sleeve simultaneously holds and protects a not shown optical fiber connecting the pattern generating member to the projector 68 for supplying light. The projector 68 is emitting a light pattern P as described above.

The pattern light source in the housing 90 is connected to a power source via the plug 90a. In the shown embodiment the power source is in form of battery casing 91 is connected to the pattern light source via an electrical conducting wire 97a for supplying power. The battery casing 91 comprises an on/off button 91'. The surgeon may use this on/off button 91' during use (training or surgery) of the surgical instrument assembly, however, for safety and to protect the battery casing 91 it is preferred that the on/off button 91' is used only at the beginning and termination of an operation, Therefore the surgical instrument assembly comprises an additional control source control unit 92 which is arranged at a distance from the surgical instrument—e. g. on the floor in form of a pedal with a control button 92', which can be operated by the surgeon during use for switching the power and thereby the light pattern on and off. The additional control source control unit 92 can be operatively connected to control the power supply in any way e.g. by being connected to the battery casing 91 via a wire 97b as shown. The housing 90 may preferably comprise additional not shown means for adjusting the pattern light source e.g. with respect to intensity, wavelength(s) and similar.

Figure 11:
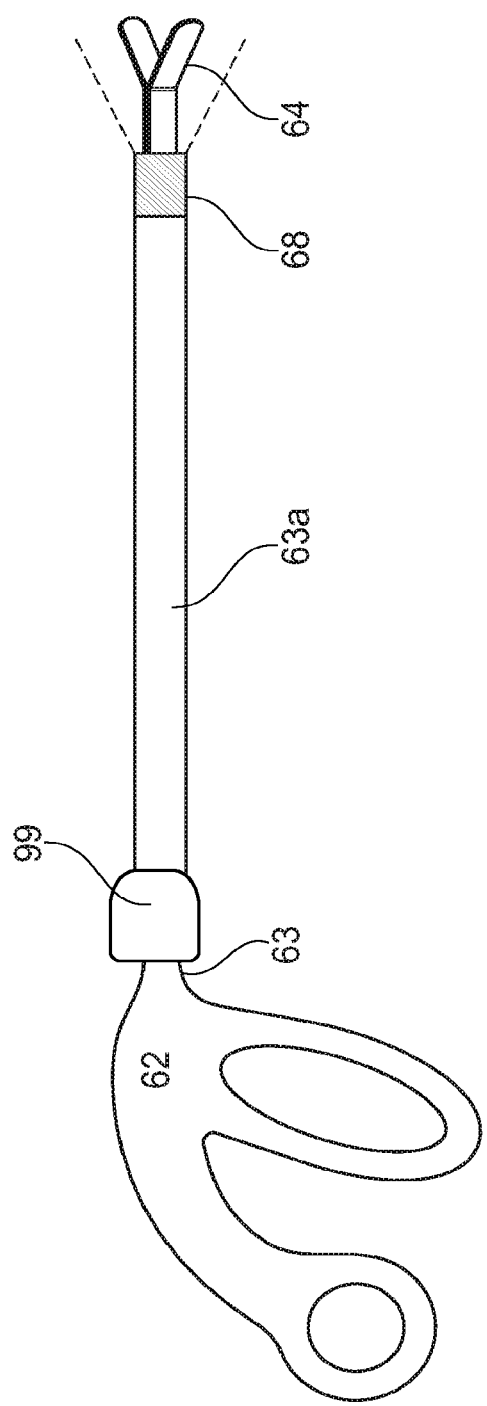
FIG. 11 illustrates a further correlated set of an embodiment of the invention comprising a surgical instrument and a pattern generating member.

The surgical instrument assembly shown in FIG. 11 is a variation of the surgical instrument assembly of FIG. 10 and differs from the embodiment of FIG. 10 in that the pattern generating member together with the power source and preferably the control unit is incorporated into the housing 99 which is mounted onto the body 63 in the same way as described for the housing 90. In this embodiment it is desired that a not shown on/off button is arranged for being manually controlled during use.

The invention claimed is:

1. An apparatus for minimally invasive surgery, comprising:
   a surgical instrument comprising a body portion and a surgical tool disposed at the distal end of the body portion; and
   a projector disposed on an exterior surface of the body portion, the projector having an outer surface including a plurality of light-emitting areas configured to project a light pattern onto tissue, the plurality of light emitting areas arranged on the outer surface such that distally-disposed light-emitting areas of the plurality of light-emitting areas project the light pattern at a first angle relative to a longitudinal axis of the body portion, and proximally-disposed light emitting areas of the plurality of light-emitting areas project the light pattern at a second angle relative to the longitudinal axis of the body portion, the second angle different from the first angle.

2. The apparatus of claim 1, wherein the projector includes at least one of a phase optic element, a spatial light modulator, a multi-order diffractive lens, a holographic lens, a Fresnel lens, a computer regulated optical element, a mirror, a filter, and a splitter.

3. The apparatus of claim 1, wherein the light pattern, when projected onto the tissue, comprises a plurality of angled lines.

4. The apparatus of claim 1, wherein the light pattern, when projected onto the tissue, comprises a grid pattern.

5. The apparatus of claim 1, wherein the projector is spherically shaped.

6. The apparatus of claim 1, wherein the projector is cylindrically shaped.

7. A surgical system, comprising:
   a surgical instrument comprising a body portion and a surgical tool disposed at the distal end of the body portion;
   a projector disposed on an exterior surface of the body portion, the projector having an outer surface including a plurality of light-emitting areas configured to project a light pattern onto tissue, the plurality of light emitting areas arranged on the outer surface such that distally-disposed light-emitting areas of the plurality of light-emitting areas project the light pattern at a first angle relative to a longitudinal axis of the body portion, and proximally-disposed light emitting areas of the plurality of light-emitting areas project the light pattern at a second angle relative to the longitudinal axis of the body portion, the second angle different from the first angle;
   a camera configured to acquire an image of the light pattern projected onto the tissue; and
   a monitor configured to display the acquired image.

8. The surgical system of claim 7, wherein the camera is an endoscope.

9. The surgical system of claim 7, wherein the camera is in data connection with a computer programmed to monitor the movements of the surgical tool of the surgical instrument.

10. The surgical system of claim 7, further comprising a computer configured to analyze the acquired image.

11. The surgical system of claim 7, wherein the camera is operatively connected to the monitor.

12. The surgical system of claim 7, wherein the projector is spherically shaped.

13. The surgical system of claim 7, wherein the projector is cylindrically shaped.

* * * * *